(12) United States Patent
Neubauer et al.

(10) Patent No.: US 11,622,903 B2
(45) Date of Patent: Apr. 11, 2023

(54) UPPER TORSO WEARABLE ORTHOTIC DEVICE WITH DYNAMIC LEVELING SYSTEM

(71) Applicant: Abilitech Medical, Inc., Eden Prairie, MN (US)

(72) Inventors: Brett Neubauer, Eagan, MN (US); Eli Krumholz, Minneapolis, MN (US); Mark Oreschnick, Inver Grove Heights, MN (US); Shawna Persaud, Apple Valley, MN (US); Rob Wudlick, Excelsior, MN (US); Tom Kramer, Andover, MN (US); Mark Manzella, Maplewood, MN (US)

(73) Assignee: Abilitech Medical, Inc., Eden Prairie, MN (US)

( * ) Notice: Subject to any disclaimer, the term of this patent is extended or adjusted under 35 U.S.C. 154(b) by 435 days.

(21) Appl. No.: 16/845,425

(22) Filed: Apr. 10, 2020

(65) Prior Publication Data
US 2020/0323724 A1 Oct. 15, 2020

Related U.S. Application Data

(60) Provisional application No. 62/831,880, filed on Apr. 10, 2019, provisional application No. 62/831,892, filed on Apr. 10, 2019.

(51) Int. Cl.
*A61H 1/02* (2006.01)
*A61F 5/01* (2006.01)

(52) U.S. Cl.
CPC ........... *A61H 1/0281* (2013.01); *A61F 5/013* (2013.01); *A61H 1/0277* (2013.01);
(Continued)

(58) Field of Classification Search
CPC ...... A61H 2201/1614; A61H 2205/062; A61F 5/013
See application file for complete search history.

(56) References Cited

U.S. PATENT DOCUMENTS 8,956,421 B2 * 2/2015 Streeter ................. A61F 2/7843
623/57
10,058,994 B2 8/2018 Angold et al.
(Continued)

FOREIGN PATENT DOCUMENTS

EP 597623 A1 5/1994
GB 2567010 A 4/2019
(Continued)

OTHER PUBLICATIONS

Ekso Innovation meets Neurorehab with EksoUE, https://eksobionics.com/eksoue/; accessed Dec. 4, 2020, 3 pages.
(Continued)

*Primary Examiner* — Samchuan C Yao
*Assistant Examiner* — Minhua Zhao
(74) *Attorney, Agent, or Firm* — Merchant & Gould P.C.

(57) ABSTRACT

An upper torso orthotic device having multiple adjustment mechanisms configured to enable adaptation to a wide variety of body shapes, sizes and augmentation needs. The upper torso orthotic device including a body worn support frame member configured to dynamically distribute a weight of the upper torso orthotic device across the chest, shoulder and back of a user, and a limb augmentation member configured to augment a native strength of an arm of the user by overcoming the effects of gravity, the limb augmentation member including an adjustable shoulder assembly including at least one of a leveling mechanism, a clavicle retraction/protraction angle adjustment mechanism, a shoulder
(Continued)

abduction angle adjustment mechanism, and a shoulder width adjustment mechanism.

17 Claims, 17 Drawing Sheets

(52) U.S. Cl.
CPC ............ *A61F 2005/0197* (2013.01); *A61H 2201/0103* (2013.01); *A61H 2201/0192* (2013.01); *A61H 2201/1253* (2013.01); *A61H 2201/165* (2013.01); *A61H 2201/1654* (2013.01)

(56) References Cited

U.S. PATENT DOCUMENTS

| | | | |
|---|---|---|---|
| 10,369,690 | B2 | 8/2019 | Van Engelhoven et al. |
| 10,391,627 | B2 | 8/2019 | Van Engelhoven et al. |
| 10,569,413 | B2 | 2/2020 | Angold et al. |
| 10,617,551 | B2 | 4/2020 | Doyle et al. |
| 10,667,938 | B2 | 6/2020 | Bonutti et al. |
| 10,918,513 | B2 | 2/2021 | Golden et al. |
| 11,253,381 | B2 | 2/2022 | Doyle |
| 2014/0158839 | A1* | 6/2014 | Doyle .................. A61B 90/60 248/118 |
| 2017/0135841 | A1 | 5/2017 | Bonutti et al. |
| 2019/0083350 | A1* | 3/2019 | Weidner ............... A61F 5/026 |
| 2019/0126795 | A1 | 5/2019 | Doyle |
| 2019/0152048 | A1 | 5/2019 | Doyle |
| 2019/0365554 | A1* | 12/2019 | Davies-Sekle ......... A61F 5/013 |

FOREIGN PATENT DOCUMENTS

| | | | | |
|---|---|---|---|---|
| WO | WO-2014024506 A1 * | 2/2014 | ............ | A61F 2/54 |
| WO | 2018111853 A1 | 6/2018 | | |
| WO | WO-2018111853 A1 * | 6/2018 | ............ | A61F 2/54 |

OTHER PUBLICATIONS

Ford Media Center, Ford Pilots New Exoskeleton Technology to Help Lessen Chance of Worker Fatigue, Injury, https://media.ford.com/content/fordmedia/fna/us/en/news/2017/11/09/ford-exoskeleton-technology-pilot.html; accessed Dec. 4, 2020, 2 pages.
Ottobock, Paexo Shoulder, https://paexo.com/paexo-shoulder/?lang=en; accessed Dec. 4, 2020, 4 pages.
Search Report dated Aug. 28, 2020 for EP Application No. 17881533.8.
Search Report and Written Opinion dated Jun. 24, 2020 for PCT Application No. PCT/US2020/027582, 9 pages.
International Preliminary Report on Patentability for Application No. PCT/US2017/065782, dated Jun. 27, 2019, 7 pages.
International Search Report and Written Opinion for Application No. PCT/US2018/021522, dated Jul. 16, 2018, 15 pages.
International Preliminary Report on Patentability for Application No. PCT/US2018/021522, dated Sep. 19, 2019, 7 pages.
International Search Report and Written Opinion for Application No. PCT/US2017/065782, dated Apr. 9, 2018, 14 pages.
Application and File history for U.S. Appl. No. 16/468,926, filed Jun. 12, 2019. Inventors: Zentgraf et al.
Application and File history for U.S. Appl. No. 16/491,509, filed Sep. 5, 2019. Inventors: Krumholz et al.
Extended European Search Report for European Application No. 20788683.9; dated Nov. 30, 2022.

* cited by examiner

UPPER TORSO WEARABLE ORTHOTIC DEVICE WITH DYNAMIC LEVELING SYSTEM

RELATED APPLICATION INFORMATION

This application claims the benefit of U.S. Provisional Application Nos. 62/831,880 (filed Apr. 10, 2019) and 62/831,892 (filed Apr. 10, 2019), both of which are fully incorporated herein by reference.

TECHNICAL FIELD

The present disclosure relates generally to systems and methods configured to assist patients or users suffering from a loss of motor skills, and more particularly to configurable upper torso wearable orthotic devices having a dynamic leveling system including multiple adjustment mechanisms enabling the upper torso orthotic devices to be adapted to a wide variety of body shapes, sizes and strength augmentation needs of patients suffering from neuromuscular disorders, spinal injuries, or impairment of limbs as a result of a stroke.

BACKGROUND

Individuals with neuromuscular abnormalities, such as neuromuscular disorders, spinal injuries, or impairment of limbs as a result of a stroke, often experience muscular atrophy and/or impaired motor function, which can lead to a loss of full functionality in their limbs and upper body. Such a loss in functionality can make the performance of routine tasks difficult, thereby adversely affecting the individual's quality of life.

In the United States alone, 1.4 million people suffer from neuromuscular disorders. It is estimated that approximately 45,000 of these people are children, who are affected by one or more pediatric neuromuscular disorders. Pediatric neuromuscular disorders include spinal muscular atrophy (SMA), cerebral palsy, arthrogryposis multiplex congenital (AMC), Becker muscular dystrophy, and Duchenne muscular dystrophy (DMD). Adult neuromuscular diseases include multiple sclerosis (MS), amyotrophic lateral sclerosis (ALS) and facio-scapulohumeral muscular dystrophy (FSHD). Many of these muscular disorders are progressive, such that there is a slow degeneration of the spinal cord and/or brainstem motor neurons resulting in generalized weakness, atrophy of skeletal muscles, and/or hypotonia.

In the United States, approximately 285,000 people suffer from spinal cord injuries, with 17,000 new cases added each year. Approximately 54% of spinal cord injuries are cervical injuries, resulting in upper extremity neuromuscular motor impairment. Spinal cord injuries can cause morbid chronic conditions, such as lack of voluntary movement, problematic spasticity, and other physical impairments which can result in a lower quality of life and lack of independence.

In the United States, it is estimated that there are over 650,000 new surviving stroke victims each year. Approximately 70-80% of stroke victims have upper limb impairment and/or hemiparesis. Numerous other individuals fall victim to silent cerebral infarctions (SCI), or "silent strokes," which can also lead to progressive limb impairment. Complications from limb impairment and hemiparesis may involve spasticity or the involuntary contraction of muscles when an individual tries to move their limb. If left untreated, the spasticity can result in the muscles freezing in abnormal and painful positions. Also, following a stroke, there is an increased possibility of developing hypertonicity, or the increased tightness of muscle tone.

People afflicted with neuromuscular abnormalities often exhibit diminished fine and gross motor skills. In cases where a person is capable of only asymmetric control of the particular joint, the person may be able to control the muscle group responsible for flexion about the joint, but his or her control over the muscle group responsible for extension may be impaired. Similarly, the opposite may be true, in that the user may have control in the extension direction, but not in the flexion direction. In either case, if the person cannot exert his or her triceps or release a hyperactive bicep, the person may be unlikely to perform the task they desire. Even in cases where a person retains symmetric control over a joint, the person may be left with reduced control over muscle groups on opposite sides of the joint. As a result, the person may be incapable of achieving the full range of motion that the joint would normally permit, and/or may be incapable of controlling the joint so that the associated limb segments exert the amount of force required to perform the desired task.

In many cases, a reduction in strength or impairment of motor function, as a result of neuromuscular abnormalities, can be slowed, stopped, or even reversed through active treatment and therapy. At least for stroke victims, data suggests that the sooner that the therapy is started after the impaired motor function is first noticed, and the greater the amount of therapy that is performed by the patient, the more likely the patient is to have a better recovery. In other cases, such as with progressive neuromuscular disorders, the goal of the treatment may be to slow the decline in functionality, so as to maintain the individual's quality of life for as long as possible. Common treatment methods include physical therapy combined with medications to provide symptomatic relief. Regarding spinal cord injuries, while there are no known treatments that can reverse morbidities, repetitive high-intensity exercise and the use of orthoses have been used to improve the strength and overall neuromuscular health of patients. Unfortunately, these kinds of therapy and exercises often utilize expensive equipment and can be limited to in-clinic settings, thereby significantly restricting the amount of therapy and its potential effectiveness.

One option to address these challenges of conventional therapy is found in upper arm support devices that have been developed to strengthen upper extremities and improve independence for accomplishing activities of daily living. Examples of advanced upper arm wearable orthoses are disclosed in Published PCT Application Nos. WO2018111853 and WO2018165413 (assigned to the Applicant of the present disclosure), the contents of which are hereby incorporated by reference herein. Although such advanced wearable orthotic systems have proven to work well, there remains a need for improvements in conformability of the orthotic systems to patients of varying body shapes, sizes and strength augmentation needs.

SUMMARY OF THE DISCLOSURE

Embodiments of the present disclosure generally provide an upper torso wearable orthotic device having multiple adjustment mechanisms configured to enable the upper torso orthotic device to be readily conformed to a wide variety of body shapes, sizes and strength augmentation needs of patients or users suffering from neuromuscular disorders, spinal injuries, or impairment of limbs as a result of a stroke is depicted in accordance with an embodiment of the disclosure. In some embodiments, the upper torso orthotic device can include a body worn support frame member configured to dynamically distribute a weight of the upper torso orthotic device across the chest, shoulder and back of a user, and a limb augmentation member configured to augment a native strength of an arm of the user by overcoming the effects of gravity. In various embodiments, the limb augmentation member can include an adjustable shoulder assembly including at least one of a leveling mechanism, a clavicle retraction/protraction angle adjustment mechanism, a shoulder abduction angle adjustment mechanism, and a shoulder width adjustment mechanism. The inclusion of some or all of these fit and/or function adjustment mechanisms, as well as other adjustment mechanisms, including the adjustment mechanisms disclosed hereinafter, is also contemplated.

One embodiment of the present disclosure provides an adjustable shoulder assembly for an upper torso orthotic device configured to enable an above shoulder mounted limb augmentation member to be operably coupled to a support frame member. The adjustable shoulder assembly can include a leveling mechanism, clavicle retraction/protraction angle adjustment mechanism, adduction angle adjustment mechanism, and shoulder width adjustment mechanism. The leveling mechanism can include structure configured to enable sliding adjustment of a limb augmentation member relative to a curved rail of a support frame member to orient the limb augmentation member relative to a gravitational frame of reference. The clavicle retraction/protraction angle adjustment mechanism can include structure configured to enable angular adjustment of the limb augmentation member relative to the support frame member to account for anatomical differences among users. The shoulder abduction angle adjustment mechanism can include structure configured to enable positioning of the limb augmentation member at a desired shoulder abduction angle relative to the support frame member. The shoulder width adjustment mechanism can include structure configured to enable lateral translation of the limb augmentation member relative to the support frame member to account for at least one of changes in the adduction angle of the limb augmentation member relative to the support frame member and/or anatomical differences among users.

In one embodiment, the leveling mechanism can include a leveling mechanism bracket slidably couplable to a curved rail of a support frame member. In one embodiment, the leveling mechanism can further include a leveling mechanism quick release member configured to enable selective locking of the leveling mechanism bracket relative to the support frame member.

In one embodiment, the wherein the clavicle retraction/protraction angle adjustment mechanism can include a first clavicle retraction/protraction angle adjustment member pivotably clavicle retraction/protraction to a second clavicle retraction/protraction angle adjustment member via at least one scapular angle adjustment fastener, wherein selective tightening of the clavicle retraction/protraction angle adjustment fastener enables locking of the first clavicle retraction/protraction angle adjustment member relative to the clavicle retraction/protraction scapular angle adjustment member. In one embodiment, the clavicle retraction/protraction angle adjustment mechanism can further include ratcheting detents configured to aid in alignment of the first clavicle retraction/protraction angle adjustment member relative to the second clavicle retraction/protraction angle adjustment member along specific angle increments.

In one embodiment, the abduction angle adjustment mechanism can include a first abduction angle adjustment member pivotably coupled to a second abduction angle adjustment member via at least one abduction angle adjustment knob, wherein selective tightening of the abduction angle adjustment knob enables locking of the first abduction angle adjustment member relative to the second abduction angle adjustment member. In one embodiment, the abduction angle adjustment mechanism can be configured to enable adjustment of the abduction angle of the limb augmentation member relative to the support frame member in discrete angle increments through a range of about 60 degrees.

In one embodiment, the shoulder width adjustment mechanism can include a first shoulder width adjustment member slidably coupled to a second shoulder width adjustment member. In one embodiment, the shoulder width adjustment mechanism can further include structure defining a slot in which a shoulder width adjustment knob is configured to traverse, wherein the shoulder width adjustment knob is configured to selectively lock the first shoulder width adjustment member in position relative to the second shoulder width adjustment member.

Another embodiment of the present disclosure provides an upper torso orthotic device having multiple adjustment mechanisms configured to enable adaptation to a wide variety of body shapes, sizes and augmentation needs. The upper torso orthotic device can include a body worn support frame and a limb augmentation member. The body worn support frame member can be configured to dynamically distribute a weight of the upper torso orthotic device across the chest, shoulder and back of a user. The limb augmentation member can be configured to augment a native strength of an arm of the user by overcoming the effects of gravity on the limb. In embodiments, the limb augmentation member can include an adjustable shoulder assembly having a leveling mechanism including structure configured to enable sliding adjustment of the limb augmentation member relative to the support frame member, a shoulder abduction angle adjustment mechanism including structure configured to enable positioning of the limb augmentation member at a desired abduction angle relative to the support frame member, and a shoulder width adjustment mechanism including structure configured to enable lateral translation of the limb augmentation member relative to the support frame.

In one embodiment, the body worn support frame member can include a body frame portion constructed of a semi-rigid material having one or more sets of living hinges configured to enable the body frame portion to readily conform to a torso of the user. In one embodiment, the body frame portion can include one or more airflow channels configured to encourage air circulation around the patient during use. In one embodiment, the body worn support frame member can include one or more inflatable bolsters configured to aid in more evenly distributing a weight of the upper torso orthotic device across the chest, shoulder and back of the user.

Another embodiment of the present disclosure provides a method of adjusting an above shoulder mounted limb augmentation member of an upper torso orthotic device relative to a support frame member, the method comprising: leveling the limb augmentation member relative to a gravitational frame of reference by sliding the limb augmentation member along a curved rail of the support frame member; adjusting a scapular angle of the limb augmentation member relative to the support frame member; adjusting a shoulder abduction angle of the limb augmentation member relative to the support frame member; and adjusting a lateral extension distances of the limb augmentation member relative to the support frame member.

Another embodiment of the present disclosure provides an upper torso augmentation system configured to augment the native strength of an arm of the user by aiding movement of the arm. The upper torso augmentation system can include an upper arm assembly, a lower arm assembly and a passive mechanism operably coupling the upper arm assembly to the lower arm assembly. The upper arm assembly can include an upper arm spring cartridge, upper arm cable, and upper arm indexing disk, wherein rotation of the upper arm indexing disk affects a spring cable tension in the upper arm assembly. The lower arm assembly can include a lower arm spring cartridge, lower arm cable and lower arm indexing disk, wherein rotation of the lower arm indexing disk affects a spring cable tension in the lower arm assembly. The passive mechanism can operably couple the upper arm assembly to the lower arm assembly and can be configured to automatically tune a spring cable tension in the lower arm assembly based on a spring cable tension in the upper arm assembly.

Another embodiment of the present disclosure provides an upper torso augmentation system configured to dynamically distribute the weight of an above shoulder mounted arm orthotic across the chest, shoulder and back of the user while the arm orthotic is in motion. The upper torso augmentation system can include a fabric garment, a support frame and an above shoulder mount for the limb augmentation device. The fabric garment can be configured to be worn around a torso of the user. The support frame member can be operably coupled to the fabric garment and can be configured to traverse from a thoracic region toward dorsum region, over a shoulder of the user. The support frame member can be constructed of a semi-rigid material including a plurality of living hinges configured to aid in the conformance of the support frame member to the body of the user during active movement. The above shoulder mount can be operably coupled to the support frame and can be configured to operably couple a limb augmentation portion to the fabric garment.

The summary above is not intended to describe each illustrated embodiment or every implementation of the present disclosure. The figures and the detailed description that follow more particularly exemplify these embodiments.

BRIEF DESCRIPTION OF THE DRAWINGS

The disclosure can be more completely understood in consideration of the following detailed description of various embodiments of the disclosure, in connection with the accompanying drawings, in which.

Figure 1:
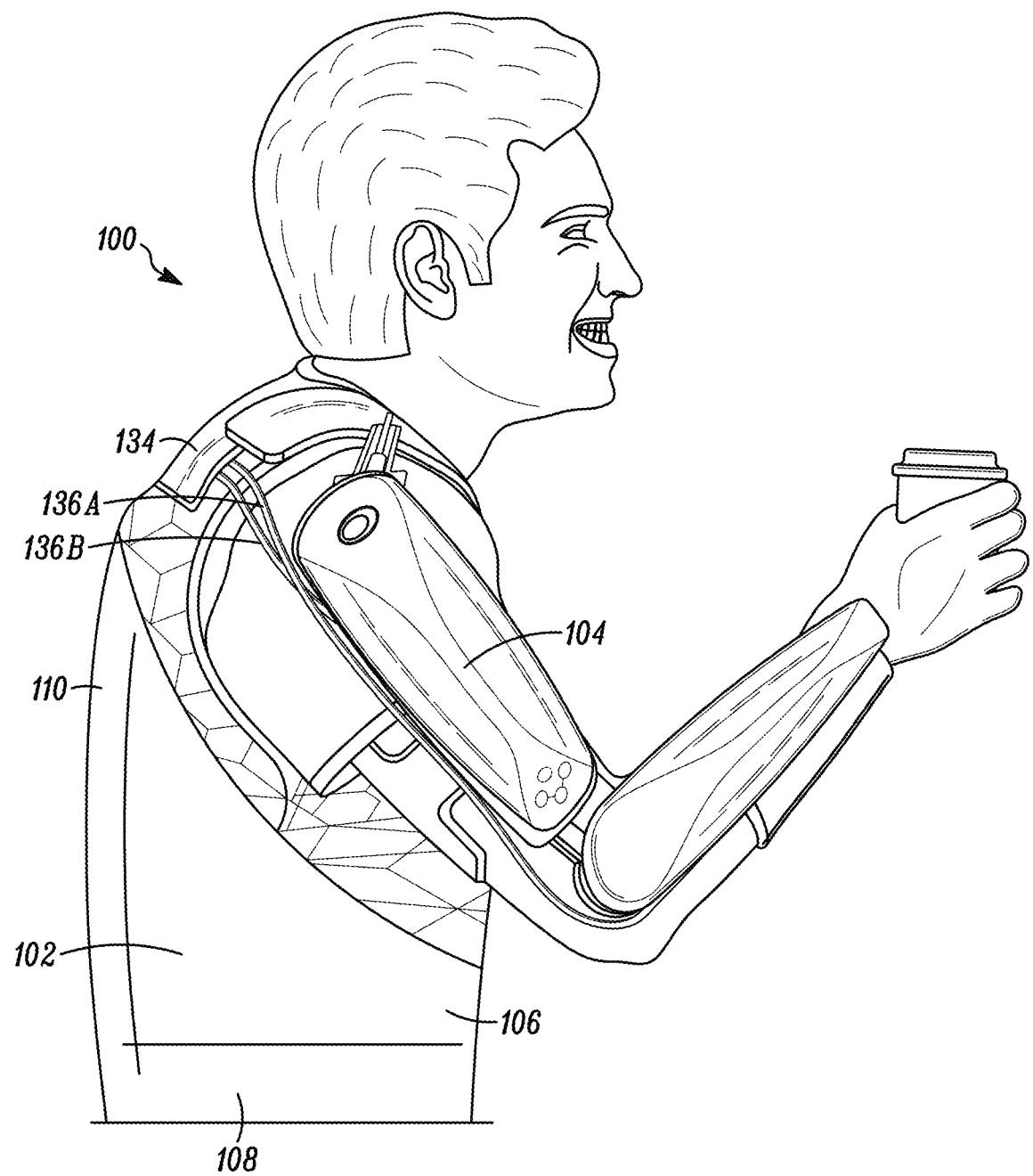
FIG. 1 is a perspective view depicting an upper torso wearable orthotic device having multiple adjustment mechanisms configured to aid in adaption of the upper torso orthotic device to a wide variety of body shapes, sizes and augmentation needs of patients or users, in accordance with an embodiment of the disclosure.

While embodiments of the disclosure are amenable to various modifications and alternative forms, specifics thereof shown by way of example in the drawings will be described in detail. It should be understood, however, that the intention is not to limit the disclosure to the particular embodiments described. On the contrary, the intention is to cover all modifications, equivalents, and alternatives falling within the spirit and scope of the subject matter as defined by the claims.

DETAILED DESCRIPTION

Referring to FIG. 1, an upper torso wearable orthotic device 100 having multiple adjustment mechanisms configured to enable the upper torso wearable orthotic device 100 to be adapted to a wide variety of body shapes, sizes and augmentation needs of patients or users suffering from neuromuscular disorders, spinal injuries, or impairment of limbs as a result of a stroke is depicted in accordance with an embodiment of the disclosure. In one embodiment, the upper torso wearable orthotic device 100 can include a support frame portion 102 and a limb augmentation portion 104. Collectively, the support frame portion 102 and limb augmentation portion 104 can be configured to counterbalance the weight of an arm of the user to serve as an aid in movement of the arm through a range of activities, while enabling a high degree of conformability to the specific anatomy of the user, as well as addressing comfort, posture and position concerns through a variety of adjustment mechanisms including adjustable brackets, angular adjustment hinges, adjustable torso supports, and the like.

In some embodiments, the support frame portion 102 can be in the form of a jacket, vest, harness, or other device, and can be configured to be worn around the torso and/or upper extremity of the user, to provide support for the user's body and connection to the limb augmentation portion 104, is depicted in accordance with an embodiment of the disclosure. In one embodiment, the support frame portion 102 is comprised of modular components for improved fit and tailored customization. For example, in one embodiment, support frame portion 102 can include, but is not limited to, a vest portion 106, a lumbar sacral orthosis (LSO) portion 108, and a body frame portion 110 configured to provide dynamic load transfer and support across a broad surface area of the user.

Figure 2:
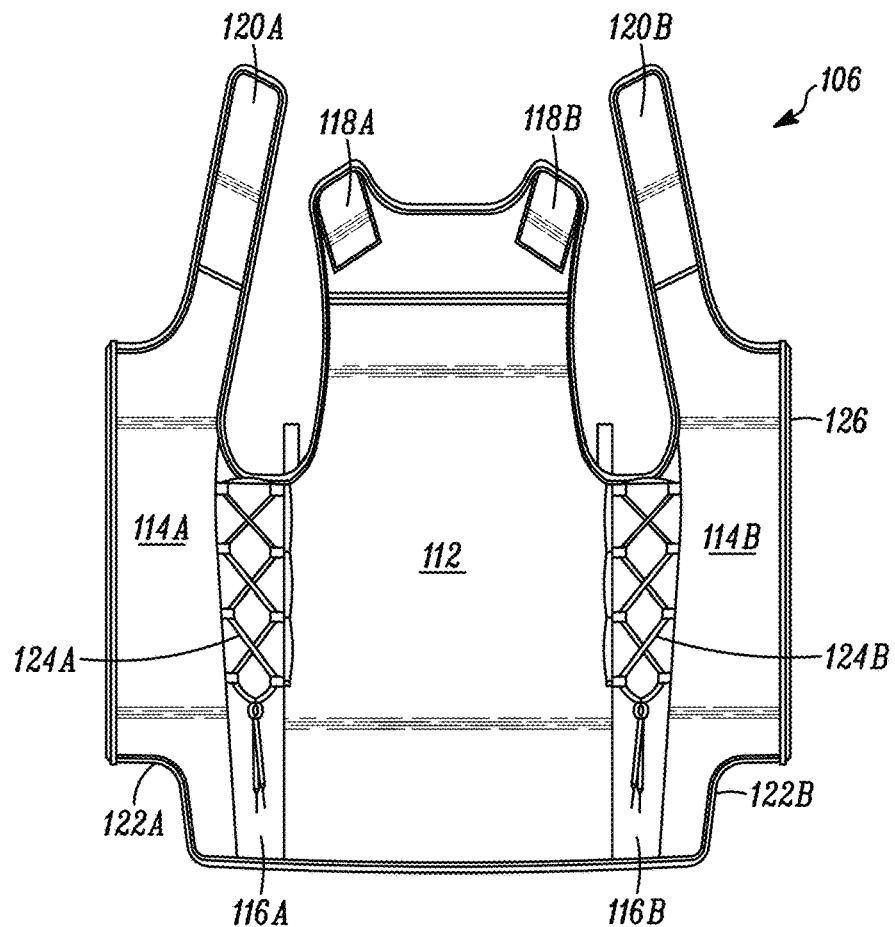
FIG. 2 is a plan view depicting a vest portion, in accordance with an embodiment of the disclosure.

With additional reference to FIG. 2, a vest portion 106 configured to conform to a variety of body shapes and sizes, is depicted in accordance with an embodiment of the disclosure. In one embodiment, the vest portion 106 can be constructed of one or more breathable, stretchable, lightweight, and/or low friction fabrics or materials. In some embodiments, the materials can be utilized in a way that mimics thermal regulation. As depicted, in some embodiments, the vest portion 106 can include a back panel 112 and a pair of front panels 114A/B operably coupled to the back panel 112 by a pair of side panels 116A/B. In one embodiment, both the back panel 112 and the front panels 114A/B can be constructed of a non-stretchable material (e.g., a textile weave), and can generally be configured to extend lengthwise from about the user's waist to about the user's shoulders. In some embodiments, both the back panel 112 and the front panels 114A/B can include one or more shoulder straps connections 118A/B, 120A/B, which can include a hook and loop fastener or other type of fastening mechanism for selective connection to one another, thereby enabling the vest portion 106 to be more easily donned and doffed by the user (e.g., without a need to thread the user's arm through an armhole). In one embodiment, the front panels 114A/B can further include structure defining respective cutout portions 122A/B in proximity to the user's waist for improved comfort when the user is in a sitting position.

In some embodiments, the pair of side panels 116A/B operably coupling the back panel 112 to the front panels 114A/B, can be constructed of a stretchable, resilient material (e.g., a polyester spandex, tricot fabric) configured to enable lateral expansion and contraction of the vest portion 106 around the torso of the user during use. In one embodiment, the vest portion 106 can further include adjustment lacing 124A/B, for example in the form of a cord, configured to inhibit lateral expansion of the vest portion 106 beyond a desired threshold. The front panels 114A/B can be selectively coupled to one another via a lateral connector 126, for example, in the form of a zipper, buttons, hook and loop fastener material, or the like.

Figure 3:
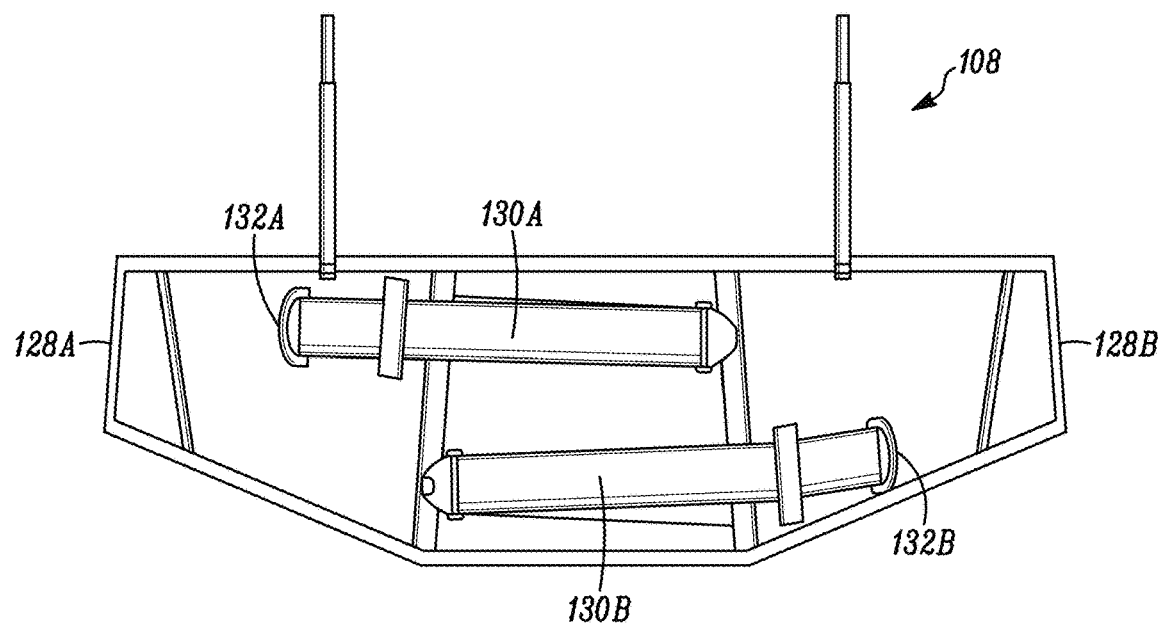
FIG. 3 is a plan view depicting a lumbar support orthotic portion, in accordance with an embodiment of the disclosure.

With additional reference to FIG. 3, an LSO portion 104 configured to conform to a variety of body shapes and sizes, is depicted in accordance with an embodiment of the disclosure. In one embodiment, the LSO portion 104 can include a lateral support panel 126 configured to wrap around a torso of the patient to provide lumbar support. In one embodiment, the lateral support panel 126 can include a first end 128A and a second end 128B configured to be operably coupled to one another, for example, via a hook and loop fastener material or other type of fastening mechanism. In some embodiments, the LSO portion 104 can further include one or more tightening straps 130A/B configured to enable further adjustment and/or fitting of the LSO portion 104 to the patient. For ease in adjustment, in some embodiments, the one or more tightening straps 130A/B can include a grip 138A/B, for example in the form of a "D" ring or other mechanism, for ease an adjustment by the patient. In other embodiments, the tightening straps 130A/B can include a quick-release lacing or cabling system, such as the BOA lacing system.

In embodiments, the vest portion 106 and/or the LSO portion 108 can be made available in a variety of sizes (e.g., X-Small, Small, Medium, Large, X-Large, 2 XL, and 3 XL) to accommodate a variety of patient chest, waist and hip sizes. Further, in some embodiments, the vest portion 106 and/or the LSO portion 108 can include one or more pockets 140 configured to stow cables 136 or other components of the upper torso orthotic device 100 (as depicted in FIG. 1). Accordingly, the vest portion 106 and LSO portion 108, which can be configured to conform to a variety of body types, shapes and sizes, can be configured to provide stabilization to the body frame portion 110. Accordingly, embodiments of the present disclosure provide a vest portion 106 and LSO portion (which in some embodiments can be collectively referred to as a "fabric garment") to closely conform to a variety of torso shapes and sizes, to dynamically distribute the weight of an above shoulder mounted limb augmentation portion 104 across the chest, shoulder and back of the user while the limb augmentation portion 104 is in motion.

Figure 4A:
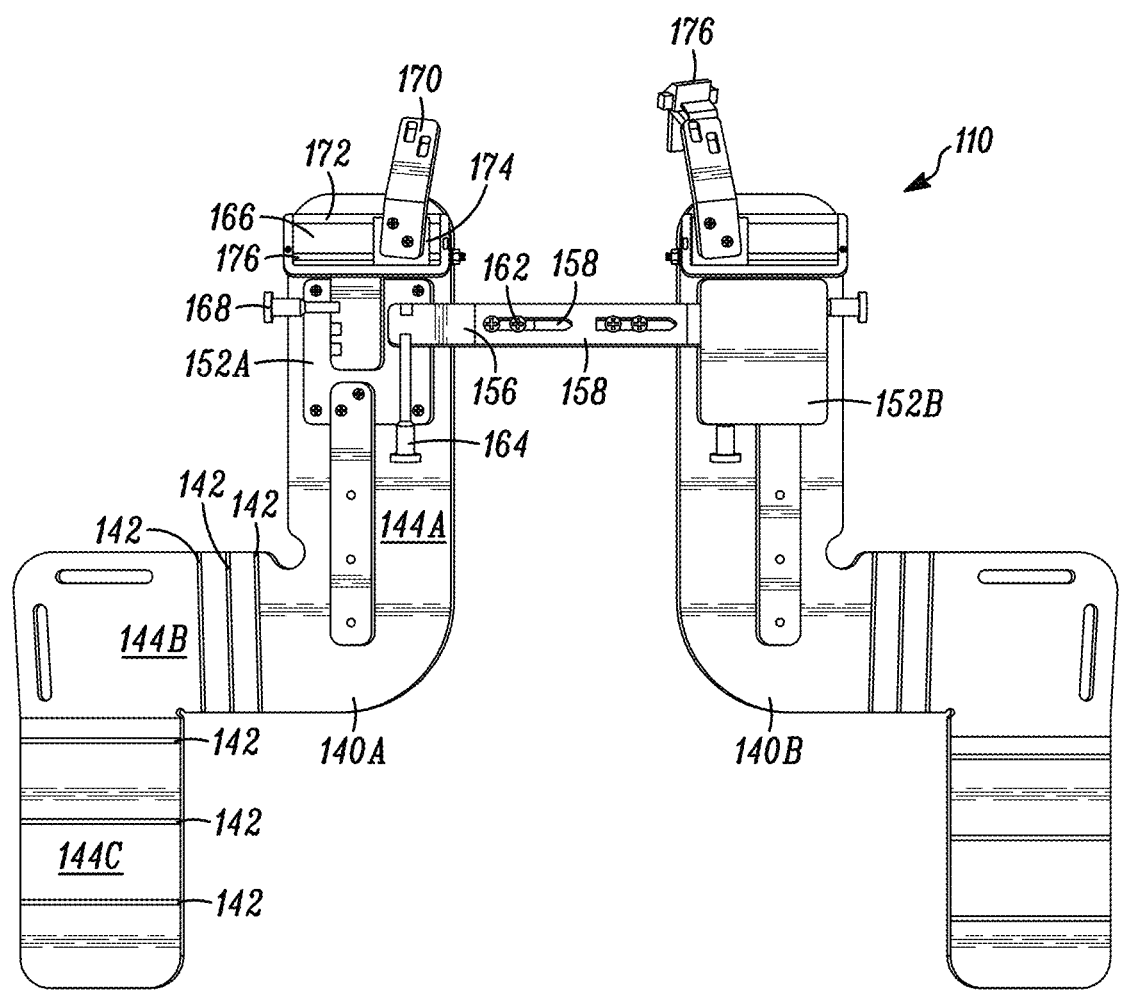
FIG. 4A is a front plan view a body frame portion configured to provide one or more mounting points for the limb augmentation portion, in accordance with an embodiment of the disclosure.
Figure 4B:
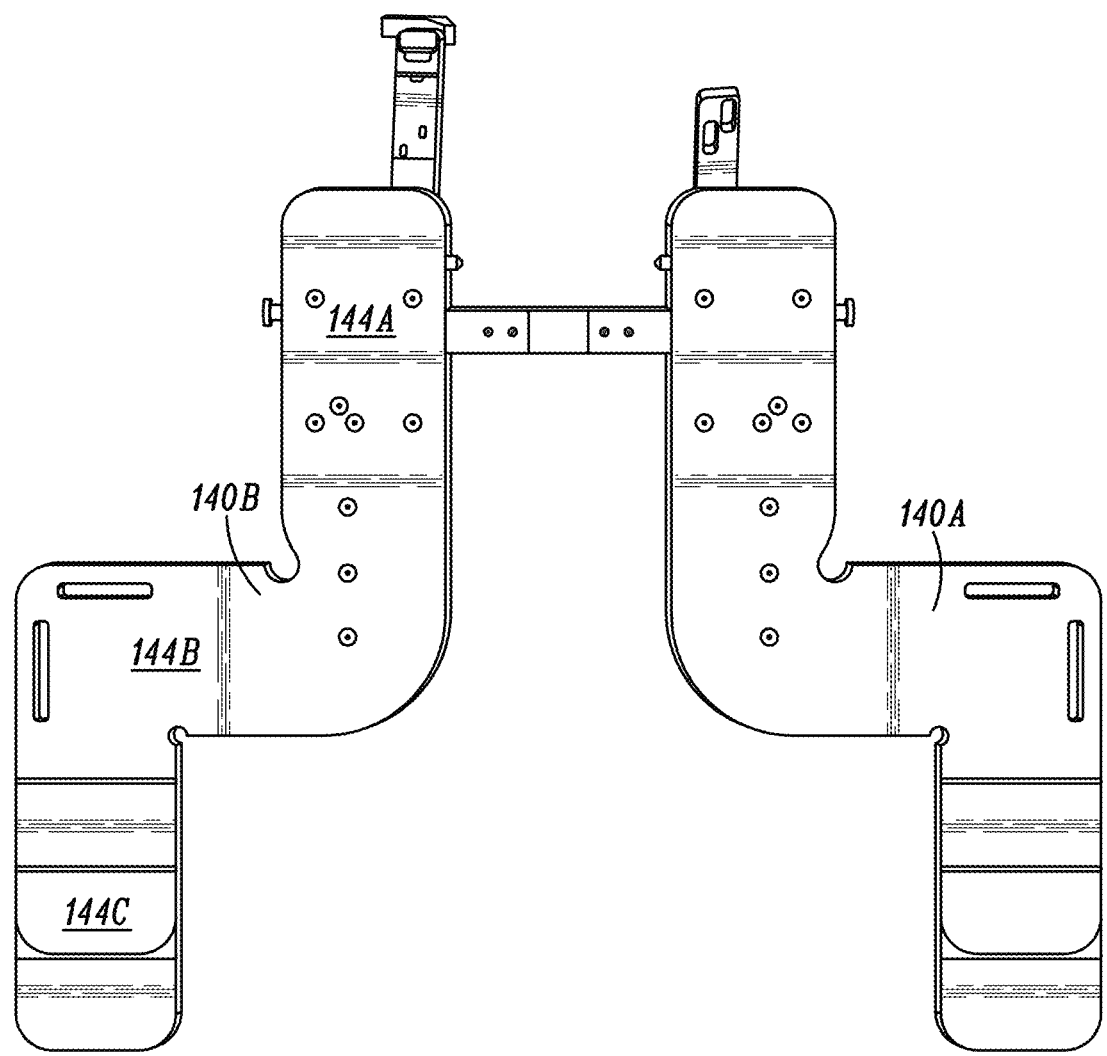
FIG. 4B is a rear plan view depicting the body frame portion of FIG. 4A.

Referring to FIGS. 4A-B, a body frame portion 110 configured provide one or more mounting points for the limb augmentation portion 104, while distributing the weight of the limb augmentation portion 104 across a broad surface of the user's torso is depicted in accordance with an embodiment of the disclosure. In one embodiment, the body frame portion 110 can include one or more semi-rigid, conformable support members 138A/B and one or more limb augmentation support members 140 A/B, which can be rigid in structure.

In one embodiment, the semi-rigid support members 138, which can be constructed out of a variety of materials (e.g., polyethylene, polypropylene, ultrahigh molecular weight plastic, compressed foam, thermoformable materials, etc.), can include one or more living hinges 142 (e.g., a thin flexure bearing point made of the same material, thereby enabling the semi-rigid support members 138 to bend along the line of the living hinge 142. For example, in one embodiment, each semi-rigid support members 138 can generally include a first longitudinal portion 144A configured to be positioned along a patient's back, a lateral portion 144B configured to conform laterally along a user's torso, and a second longitudinal portion 144C configured to extend downwardly along the user's side towards the user's pelvis. As depicted in FIGS. 4A-B, in one embodiment, a set of three living hinges 142 can be positioned along the lateral portion 138B for improved conformability around the patient's torso, and a set of three living hinges 142 can be positioned along the second longitudinal portion 138C for improved conformability to the user's hips. Additionally, in some embodiments, one or more living hinges 142 can be positioned along the first longitudinal portion 144A. Alternate placement and/or the inclusion of a greater or lesser number of living hinges are also contemplated. In one embodiment, the length of the respective first longitudinal portion 144A, lateral portion 144B, and second longitudinal portion 144C can be selected or adjusted to accommodate patients of different shapes and sizes.

Figure 5:
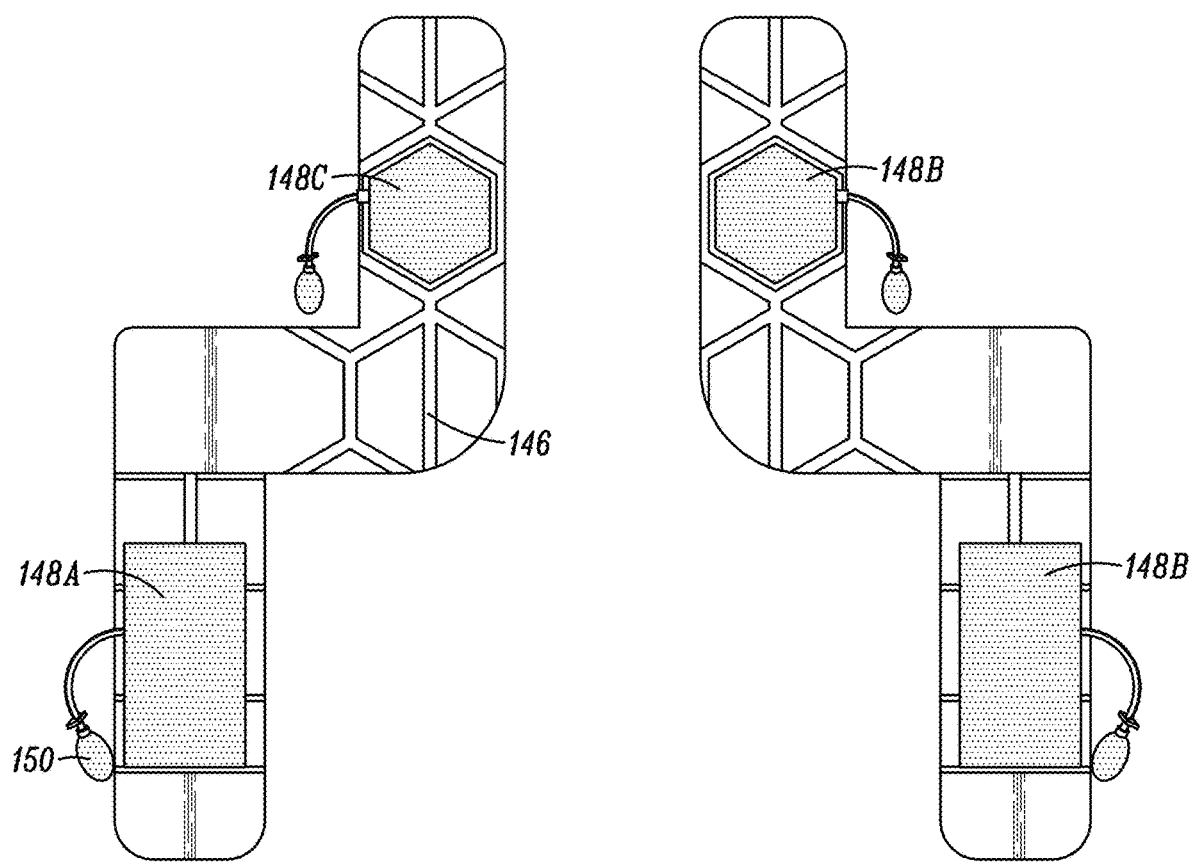
FIG. 5 is a plan view depicting the semi-rigid support member including one or more airflow channels and one or more inflatable bolsters, in accordance with an embodiment of the disclosure.

In some embodiments, the living hinges 142 can be included in both the front and back surface of the semi-rigid support member 138. In other embodiments, the living hinges 142 can be positioned on a single side of the semi-rigid support member 138 for use in manufacturing. With additional reference to FIG. 5, in some embodiments, the semi-rigid support members 138 can include one or more airflow channels 146 configured to improve circulatory airflow around the patient and/or breathability of the support frame portion 102, as well as increased flexibility for patient support and comfort. For example, in some embodiments, the one or more airflow channels 146 can additionally act as a living hinge. Further, in some embodiments, the semi-rigid support members 138 can include one or more bolsters 148A-D, for example in the form of an inflatable bladder, for improved lateral stability (e.g., bolsters 148A/B) and scapular support (e.g., bolsters 148C/D). Accordingly, the bolsters 148 can be configured to more evenly distribute the weight of the upper torso orthotic device 100 across the chest, shoulder and back of the user, particularly while the limb augmentation portion 104 is in motion. In some embodiments, the bolsters 148 can be helpful in reducing the likelihood of a patient developing pressure sores, particularly for users with dysmorphic scapula, scoliosis, and other conditions which may tend to focus pressure on a particular portion of the user's upper body. As depicted, the one or more bolsters 148 can be inflated manually, for example via a bulb 150. Alternatively, the one or more bolsters 148 can be activated dynamically via one or more integrated sensors and/or activation switches.

With continued reference to FIG. 4A, the limb augmentation support member 140 can include one or more shoulder junction box 152, which can be operably coupled to the semi-rigid support member 138, for example with the aid of one or more back rail 154. In some embodiments, a variety of different length back rails 154 can be provided to accommodate patients of different sizes.

A back connecting bracket 156 can operably couple a left and right shoulder junction boxes 152A/B, thereby coupling the left and right sides of the body frame portion 110 to one another. In some embodiments, the back connecting bracket 156 can include a lateral adjustment mechanism 158, such as a slot 160 and one or more fastener 162, thereby enabling a lateral adjustment of a connection between the left and right shoulder junction boxes 152A/B to accommodate for varying shoulder widths of patients. For improved modularity, in some embodiments, a quick release 164 can be provided to enable ease in disconnection of the one or more shoulder junction boxes 152A/B from the back connecting bracket 156.

In some embodiments, the limb augmentation support member 140 can further include one or more shoulder bracket 166 configured to be operably coupled to the shoulder junction box 152. For improved modularity and adaptability, in some embodiments, a quick release/height adjustment mechanism 168 can be provided to enable an adjustment in the height of the shoulder bracket 166 relative to the shoulder junction box 152, as well as ease in disconnection of the shoulder bracket 166 from the one or more shoulder junction box 152. For example, in one embodiment, the quick release 168 can be configured to enable a vertical height adjustment in three discrete increments; although a greater or lesser number of adjustment increments and/or adjustment over a continuous range of vertical heights is also contemplated.

A shoulder rail 170 can be operably coupled to the shoulder bracket 166. For example, in one embodiment, the shoulder rail 170 can be operably coupled to the shoulder bracket 166 via a shoulder positioning mechanism 172, for example an angled block 174 and threaded fastener 176. Accordingly, in some embodiments, rotation of the threaded fastener 176 can cause lateral translation of the angled block 174 within the shoulder bracket 166, thereby enabling lateral positioning of the shoulder rail 170 for customization of the body frame portion 110 to accommodate patients of a variety of shapes and sizes.

For improved leveling of the limb augmentation portion 104 with respect to a gravitational frame of reference, in some embodiments, the angled block 174 can be configured to couple the shoulder rail 170 to the shoulder bracket 166 at a slight angle (e.g., at a 5° offset from a longitudinal centerline). In some embodiments, the limb augmentation portion 104 can be configured to couple to a dovetail rail 176, which can be positioned on the shoulder rail 170.

Accordingly, embodiments of the support frame portion 102 provide a modular design that enables the selection of a range of sizes of components to accommodate the anatomy of a patient, as well as multiple quick release and adjustment mechanisms to enable customization of the support frame portion 102 for improved comfort and fit. In particular, embodiments of the present disclosure enable a selection of different sizes of the vest portion 106, lumbar sacral orthosis portion 108, semi-rigid support members 138A/B, and back rails 154A/B in assembly of the support frame portion 102. Once assembled, the body frame portion 110 of the support frame portion 102 may be adjustable via one or more of a lateral adjustment mechanism 158 (configured to enable an adjustment in the length of the back connecting bracket 156 separating the shoulder junction boxes 152A/B), a height adjustment mechanism 168 (configured to enable an adjustment in the height of the shoulder bracket 166 relative to the shoulder junction box 152), and shoulder positioning mechanism 172 (configured to enable lateral adjustment of the shoulder rail 170 relative to the shoulder bracket 166). Additionally, embodiments of the present disclosure enable quick release of the back connecting bracket 156 from the shoulder junction box 152 (via quick release 164), as well as quick release of the shoulder bracket 166 from the shoulder junction box 152 via quick release 168. Other sizes of modular components, adjustment mechanisms, and quick releases are also contemplated.

Figure 6A:
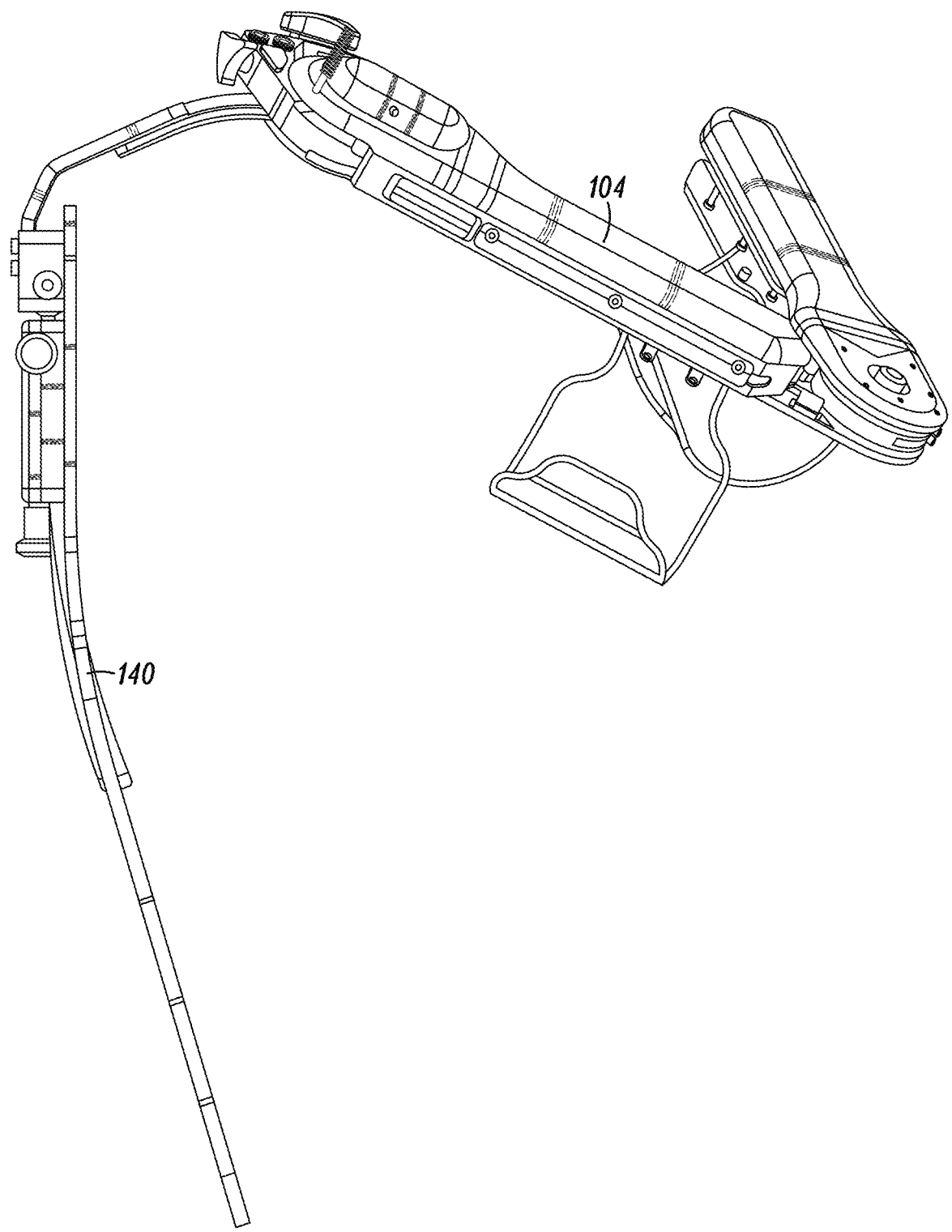
FIG. 6A is a side, perspective view depicting a limb augmentation portion operably coupled to a limb augmentation support member of a support frame portion, in accordance with an embodiment of the disclosure.
Figure 6B:
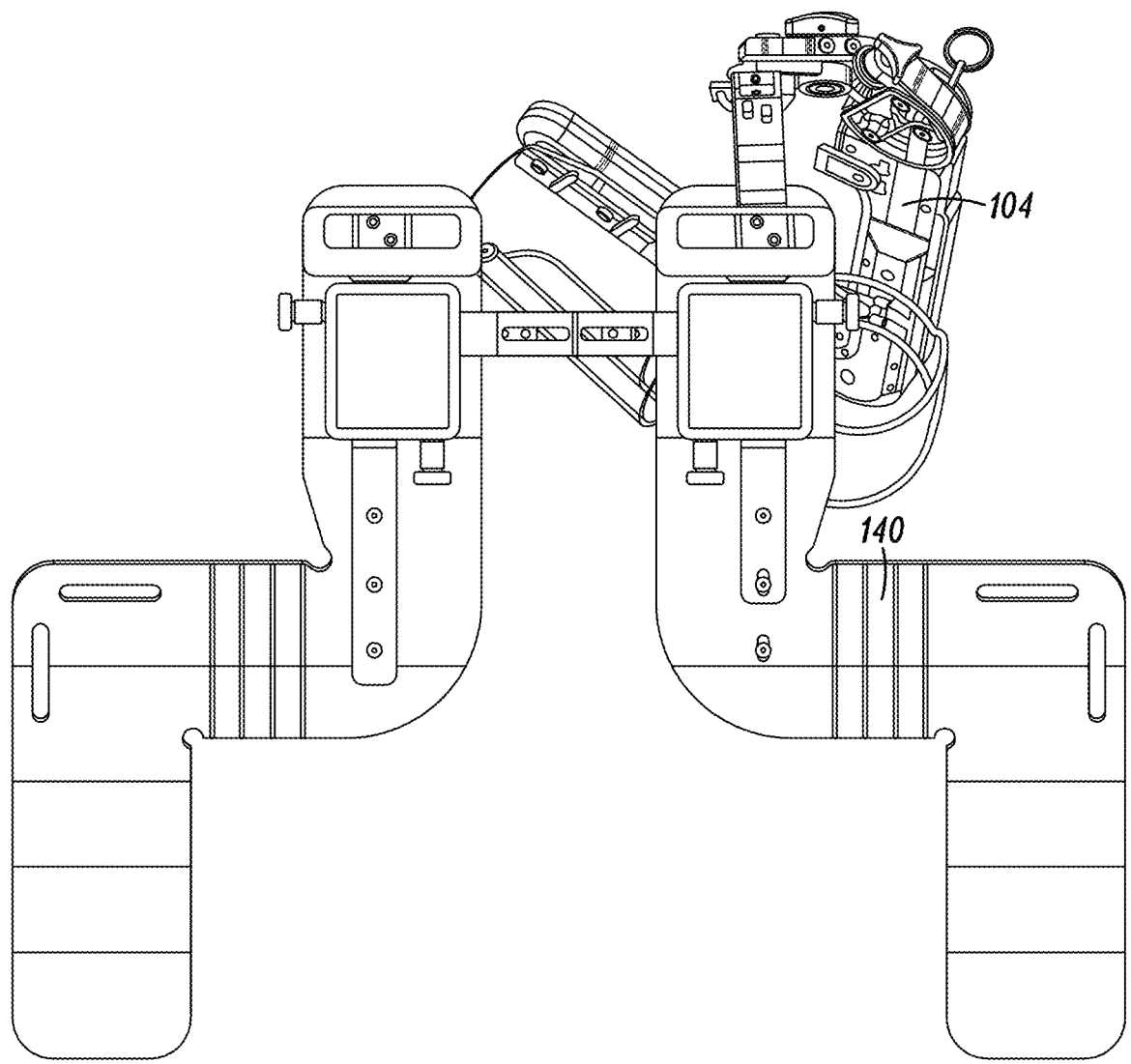
FIG. 6B is a rear, perspective view depicting the limb augmentation portion operably coupled to the limb augmentation support member of FIG. 6A.

Referring to FIGS. 6A-B, a limb augmentation portion 104 operably coupled to the limb augmentation support member 140 of the support frame portion 102, is depicted in accordance with an embodiment of the disclosure. In one embodiment, the limb augmentation portion 104 is configured to counterbalance the weight of an arm of the user to overcome the effects of gravity, and in some cases to aid in movement of the arm through a range of motions.

Figure 7:
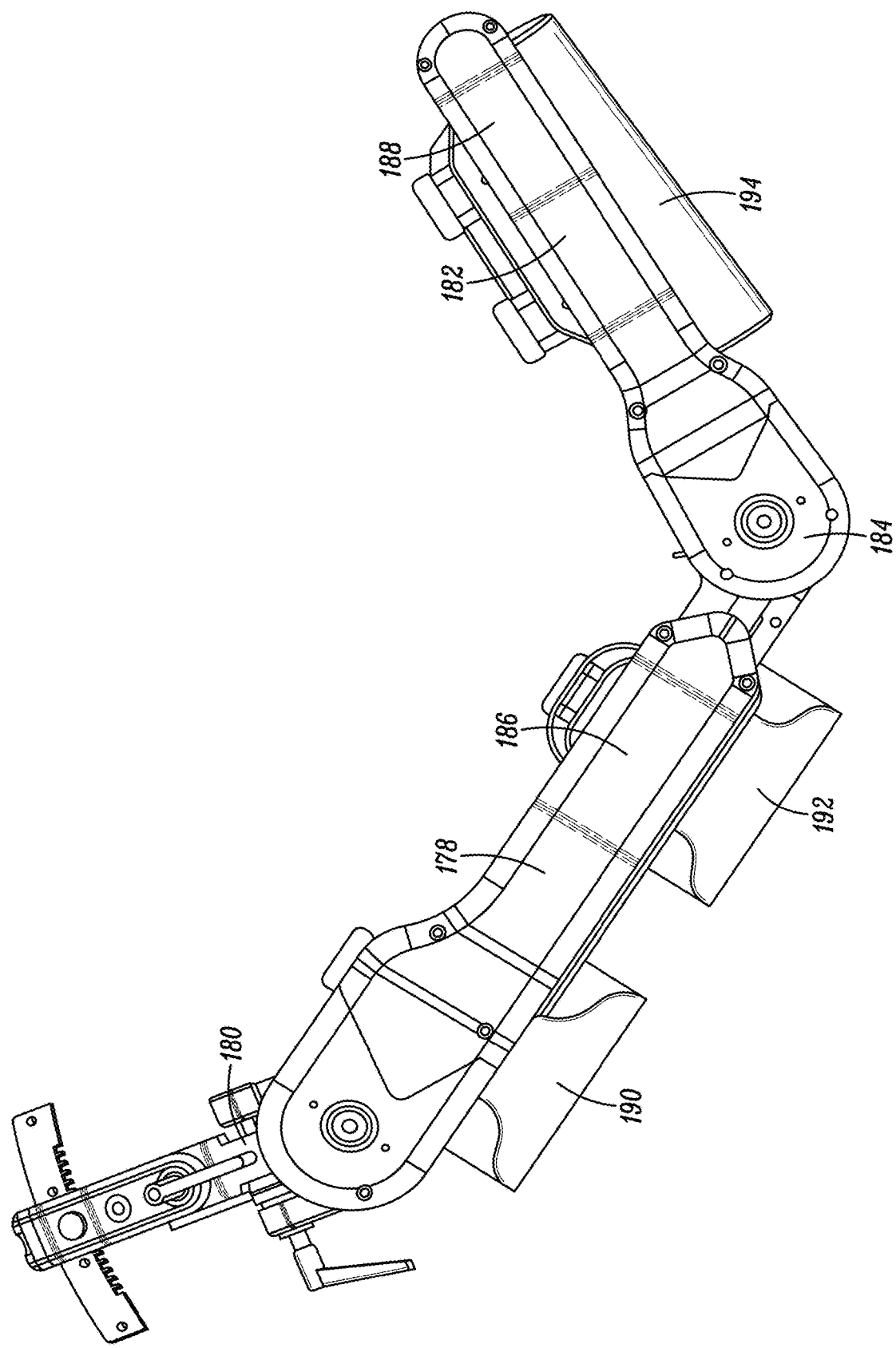
FIG. 7 is a profile view depicting a limb augmentation portion, in accordance with an embodiment of the disclosure.

With additional reference to FIG. 7, in one embodiment, the limb augmentation portion 104 can include an upper arm assembly 178 pivotably coupled to a shoulder assembly 180. An optional lower arm assembly 182 can be pivotably coupled to the upper arm assembly 178 via an elbow assembly 184. In some embodiments, at least one of the upper arm assembly 178 and/or lower arm assembly 182 can include an assisted force mechanism 186, 188 (as further described in connection with FIGS. 8-10), wherein an output of the assisted force mechanism 186, 188 is adjustable, thereby enabling an output of the assisted force mechanism 186, 188 to approximate a determined minimum assist force required for the patient to move their arm through a desired range of motion so as to minimize any excess torque produced by the limb augmentation portion 104 necessary to overcome the effects of gravity.

As further depicted in FIG. 7, in some embodiments, the limb augmentation portion 104 can include one or more cuffs 190, 192 & 194 configured to support portions of a user's arm in connection to the limb augmentation portion 104 as well as to transfer motion of the limb augmentation portion 104 into the human body. In one embodiment, the one or more cuffs can include a humeral cuff 190, elbow cuff 192, and a forearm cuff 194. For improved adaptability and conformability of the upper torso orthotic device 100 to a wide variety of patient shapes and sizes, a variety of cuff sizes and shapes can be provided. Additionally, embodiments of the present disclosure can enable adjustment in the positioning of the cuffs 190, 192 & 194 for improved fitting of the limb augmentation portion 104 to the body of a patient.

Figure 8:
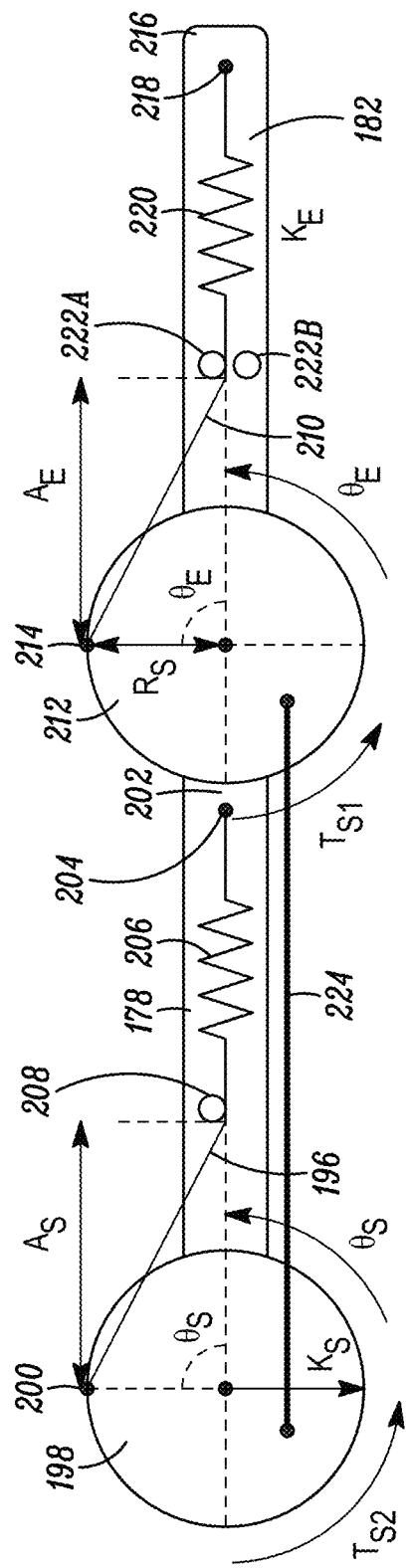
FIG. 8 is a schematic diagram depicting a limb augmentation portion, in accordance with an embodiment of the disclosure.

Referring to FIG. 8, a schematic diagram of a limb augmentation portion 104 is depicted in accordance with an embodiment of the disclosure. In one embodiment, the upper arm assembly 178 can include a tension cable 196 anchored to an indexing disk 198 at a first end 200 and to a distal end 202 of the upper arm assembly 178 at a second end 204 via a spring 206. In some embodiments, the tension cable 196 can travel around one or more bearings 208 or pulleys between the first end 200 and the second end 204.

Similarly, the optional lower arm assembly 182 can include a tension cable 210 anchored to an indexing disk 212 at a first end 214 and to a distal end 216 of the lower arm assembly 182 at a second end 218 via a spring 220. In some embodiments, the tension cable 210 can travel around one or more bearings 222 or pulleys between the first end 214 and the second end 218. For example, in one embodiment, a pair of bearings 222A/B can be utilized to enable rotation of the lower arm assembly 182 beyond an angle at which the tension cable 210 would no longer be constrained by a single bearing 220A.

In some embodiments, a connecting rod 224 operably coupling the upper arm indexing disk 198 to the lower arm indexing disk 212 can be configured to rotate the lower arm indexing disk 212 based on the position of the upper arm indexing disk 198, thereby increasing or decreasing a tension in the lower arm tension cable 210 based on a shoulder rotation position (e.g., a lateral position with respect to a gravitational reference) of the upper arm assembly 178. For example, in some embodiments, the first indexing disk 198 can be configured to maintain its position with respect to a gravitational frame of reference, regardless of the shoulder rotation of the user and subsequent position of the upper arm assembly. Operably coupling the first indexing disk 198 to the second indexing disk 212 via the connecting rod 224, thus forces the second indexing disk 212 to also maintain its position with respect to a gravitational frame of reference. Accordingly, in some embodiments, the connecting rod 224 is configured to ensure that a counterbalance force of the lower arm assembly 182 (e.g., a tension preload in the lower arm spring 220) is adjusted based on a shoulder angle of the user.

Figure 9:
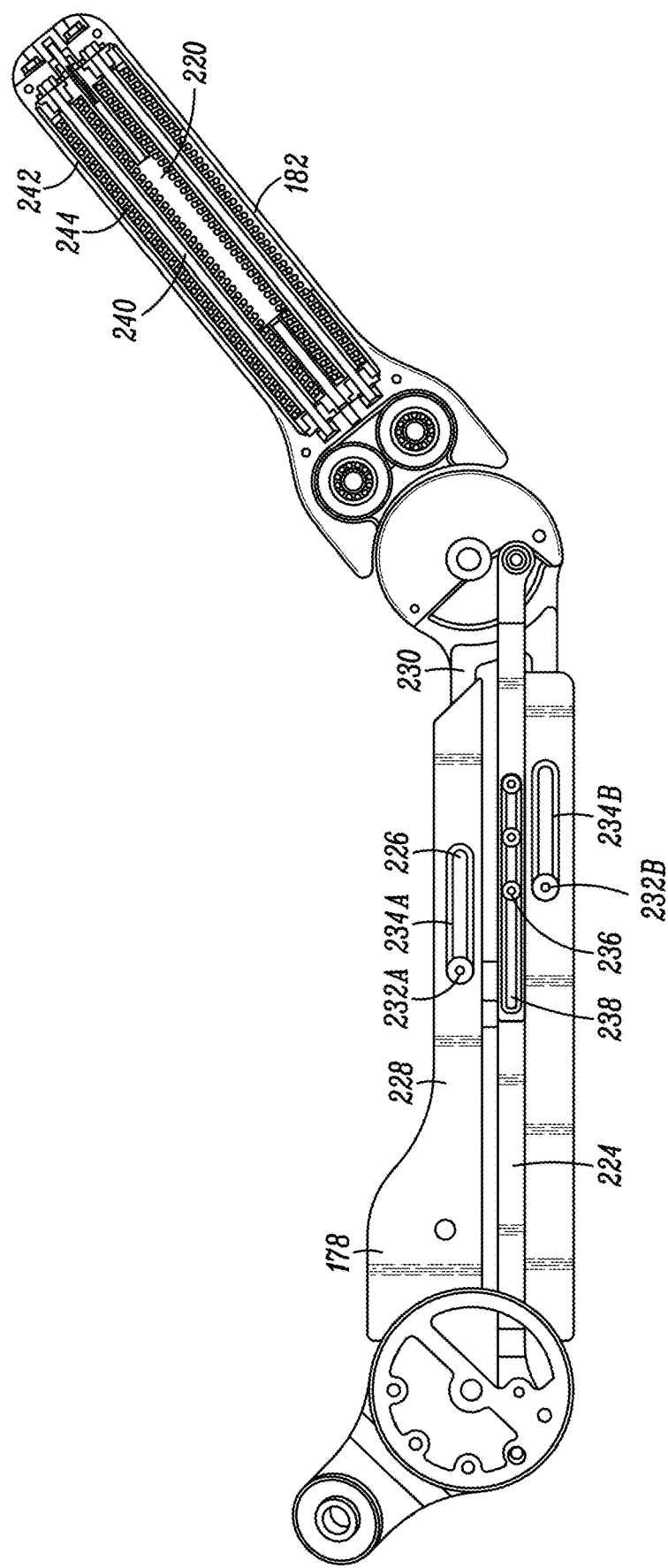
FIG. 9 is a profile view depicting a limb augmentation portion including a humeral length adjustment mechanism, in accordance with an embodiment of the disclosure.

With additional reference to FIG. 9, for the purpose of improving adaptability of the upper torso wearable orthotic device 100 a variety of patient shapes and sizes, in some embodiments the upper arm assembly 178 can be configured to be adjustable in length via a humeral length adjustment mechanism 226. For example, in one embodiment, the upper arm assembly 178 can be comprised of a first portion 228 and a second portion 230. One or more fasteners 232A/B can operably couple the first portion 228 to the second portion 230. To enable a sliding length adjustment of the upper arm assembly 178, in some embodiments, either of the first portion 228 and/or the second portion 230 can include structure defining a slot 234A/B in which the one or more fasteners 232A/B can traverse. Fixing a length of the upper arm assembly 178 can be established by sliding the first portion 228 relative to the second portion 230 until a desired length of the upper arm assembly 178 is established, then tightening the one or more fasteners 232, thereby locking the first portion 228 relative to the second portion 230. A similar mechanism, including one or more fasteners 236 and slot 238 can be included on the connecting rod 224.

The springs 206, 220 in the upper and lower arm assemblies 178, 182 can be configured to apply a force sufficient to counterbalance the effects of gravity on the arm of the user (as well as any item in a hand of the user). For example, in one embodiment, springs 206, 220 can be configured with one or more springs of different K factors appropriately sized for the weight and/or length of the user's arm. In some embodiments, the spring 220 for the lower arm assembly 182 can have a K factor of approximately ¼ of a K factor of the spring cartridge 206 for the upper arm assembly 178.

Figure 10:
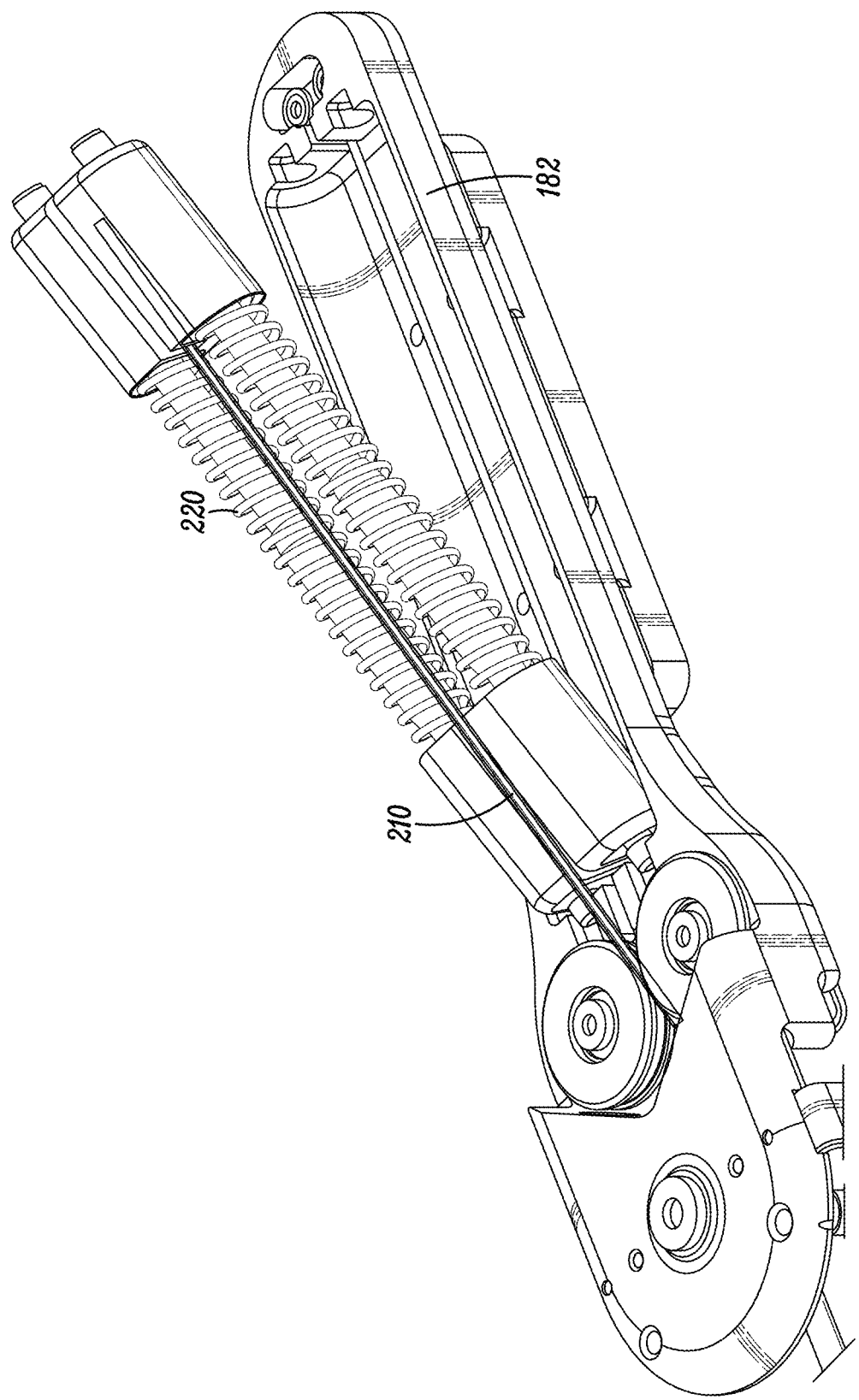
FIG. 10 is a perspective view depicting a lower arm assembly in which one or more replaceable spring cartridges can be installed, in accordance with an embodiment of the disclosure.

With additional reference to FIG. 10, in some embodiments the springs 206, 220 can be configured as replaceable spring cartridges, thereby enabling improved adaptability of the upper torso orthotic device 100 to meet the needs of a variety of patients strengths in the performance of a variety of given tasks. For example, if the patient is using the upper torso orthotic device 100 to pick up relatively heavy objects (e.g., a bottle of water), replaceable spring cartridges having a higher overall K factor (e.g., stiffer springs) can be utilized. By contrast, if the patient is using the upper torso orthotic device 100 to type on a keyboard, where no object is being picked up, the replaceable spring cartridges can have a lower overall K factor.

As best depicted in FIG. 9, in some embodiments, the spring cartridges 206, 220 can include one or more rods 240, having one or more springs 242, 244 surrounding the one or more rods 240. As depicted, in one embodiment, the spring cartridges 206, 220 can include a pair of rods 240, having a first set of springs 244 coaxially positioned within a second set of springs 242; although other spring cartridge configurations having a greater or lesser number of rods and springs are also contemplated. For example, in one embodiment, the spring cartridge can include four rods with a single spring coaxially positioned around each rod. In some embodiments, a first spring 242 of each coaxial arrangement can be wound in an opposite direction to a second spring 244, thereby limiting interference between the springs 242, 244.

Figure 11:
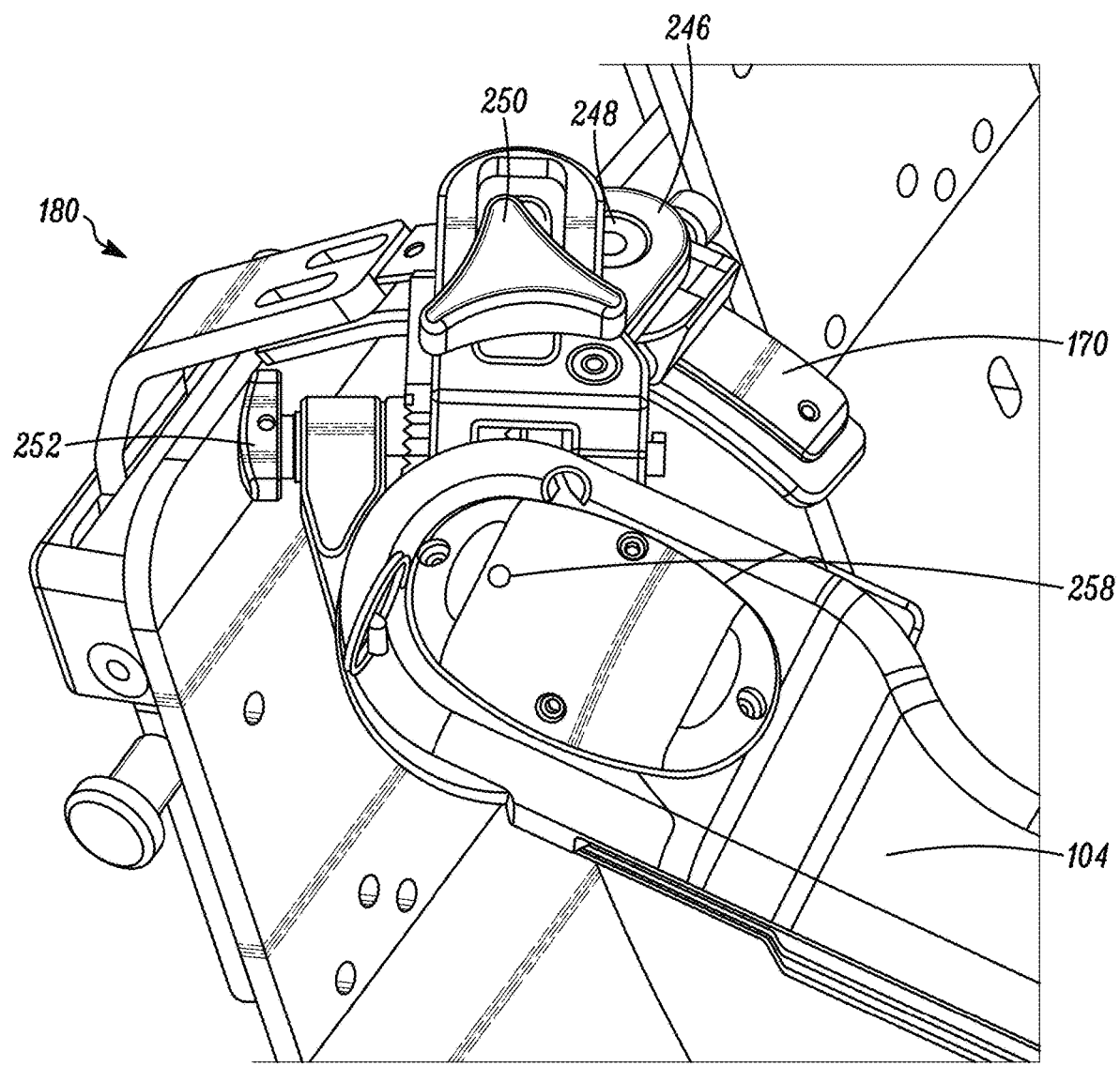
FIG. 11 is a perspective view depicting a shoulder assembly including a leveling mechanism, clavicle retraction/protraction angle adjustment mechanism, shoulder width adjustment mechanism, and shoulder abduction/abduction angle adjustment mechanism, in accordance with an embodiment of the disclosure.

Referring to FIG. 11, a perspective view of a shoulder assembly 180 is depicted in accordance with an embodiment of the disclosure. In some embodiments, the shoulder assembly 180 can include multiple adjustment mechanisms configured level the limb augmentation portion 104 relative to a gravitational frame of reference, as well as to adapt the overall fit of the upper torso wearable orthotic device 100 to the specific anatomy of a patient. For example, in some embodiments, the shoulder assembly 180 can include an optional leveling mechanism 246 (as further depicted in FIG. 12), an optional clavicle retraction/protraction angle adjustment mechanism 248 (as further depicted in FIG. 13), an optional shoulder width adjustment mechanism 250 (as further depicted in FIG. 14), and an optional shoulder abduction/adduction angle adjustment mechanism 252 (as further depicted in FIG. 15).

Figure 12:
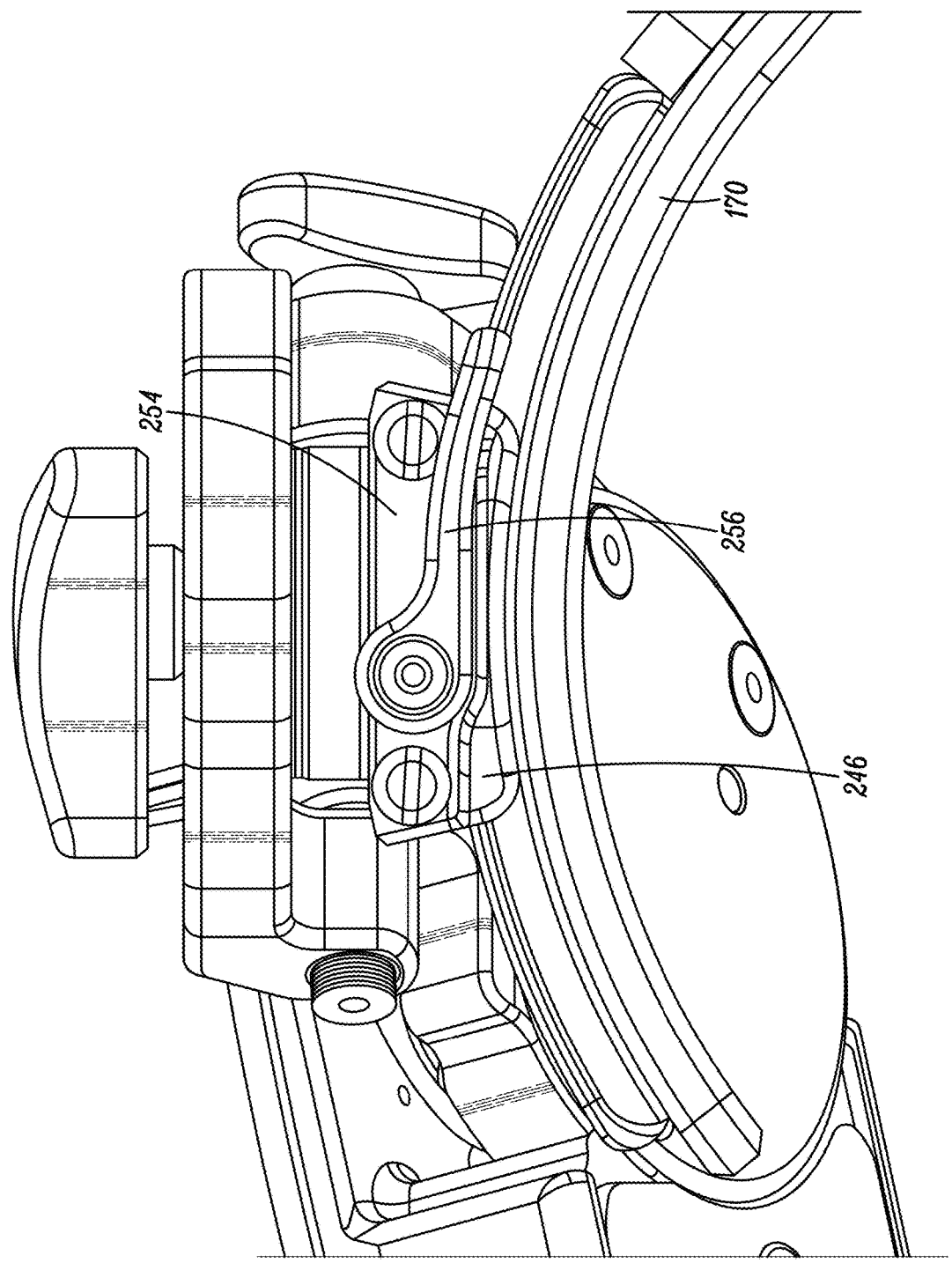
FIG. 12 is a close-up view depicting the leveling mechanism of FIG. 11.

With additional reference to FIG. 12, the leveling mechanism 246 can include a bracket 254 configured to slidably coupled to the curved shoulder rail 270 of the limb augmentation support member 140. In some embodiments, the bracket 254 can include a quick release member 256 configured to enable ease in sliding adjustment of the bracket 254 relative to the curved shoulder rail 170, such that manipulation of the quick release member 256 can lock the bracket 254 in position relative to the curved shoulder rail 170. Accordingly, in some embodiments, the leveling mechanism 246 can be configured to enable the limb augmentation portion 104 to be leveled relative to a gravitational frame of reference, thereby enabling a gravity neutral pivoting of the limb augmentation portion 104 about a shoulder pivot 258 (as depicted in FIG. 11). Thus, embodiments of the present disclosure enable adjustment of the upper torso orthotic device 100 to account for the effects that a user's posture or position may have on assisted manipulation of their arm through a desired range of motions via the limb augmentation portion 104.

Figure 13:
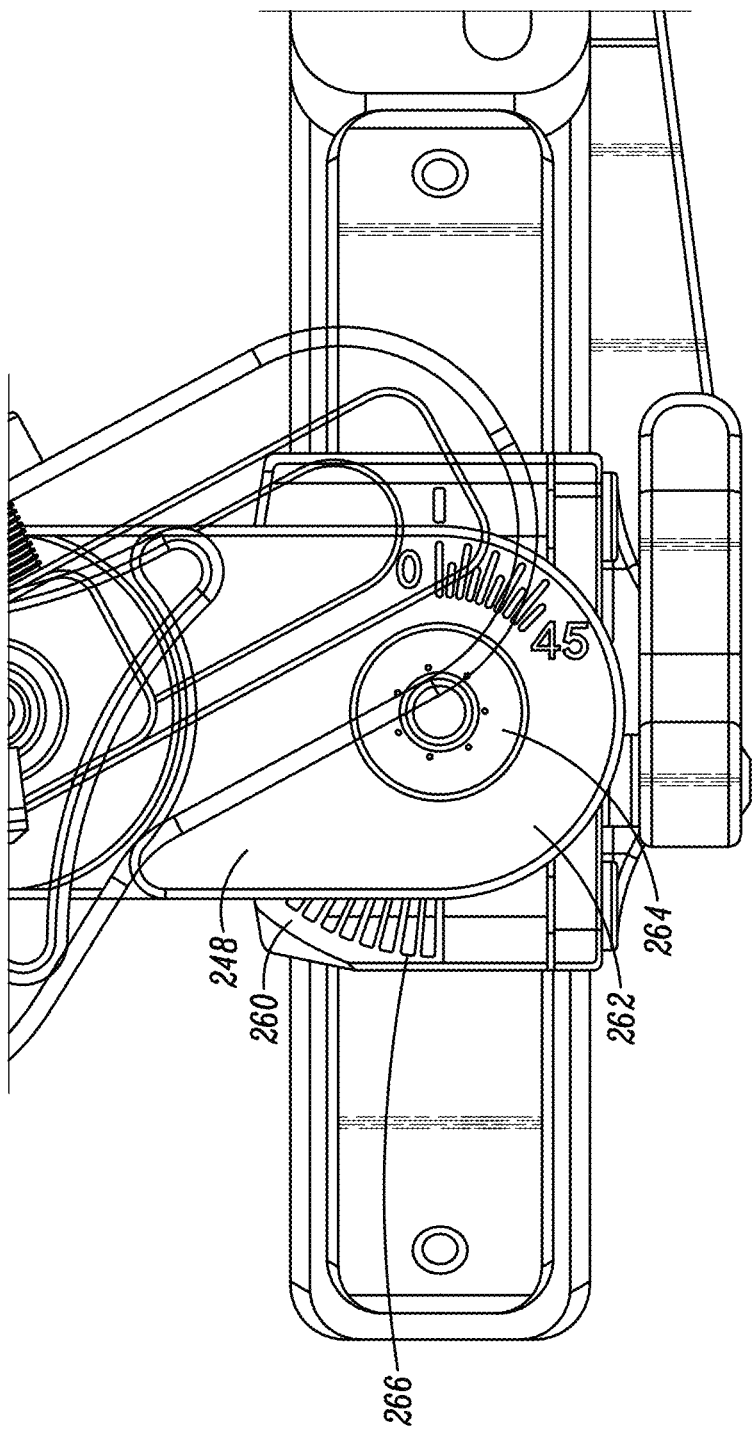
FIG. 13 is close-up view depicting the clavicle retraction/protraction angle adjustment mechanism of FIG. 11.

With additional reference to FIG. 13, the clavicle retraction/protraction angle adjustment mechanism 248 can include a first member 260 operably coupled to a second member 262, for example via a fastener 264. In some embodiments, at least one of the first member 260 and/or second member 262 can include ratcheting detents 266 configured to aid in alignment of the first member 260 relative to the second member 262 along specific angle increments. An angle of the first member 260 relative to the second member 262 can be locked in position, for example via tightening of the fastener 264. Accordingly, in some embodiments, an angular extension of the limb augmentation portion 104 outwardly from the limb augmentation support member 140 can be adjusted to fit in order to account for varying scapular angles and other physiological differences in patients. In one embodiment, the scapular angle is adjustable across a range of about 45° as an aid in aligning a center of the shoulder rotation of the limb augmentation portion 104 with the anatomy of the patient; although other angular adjustment ranges are also contemplated.

Figure 14:
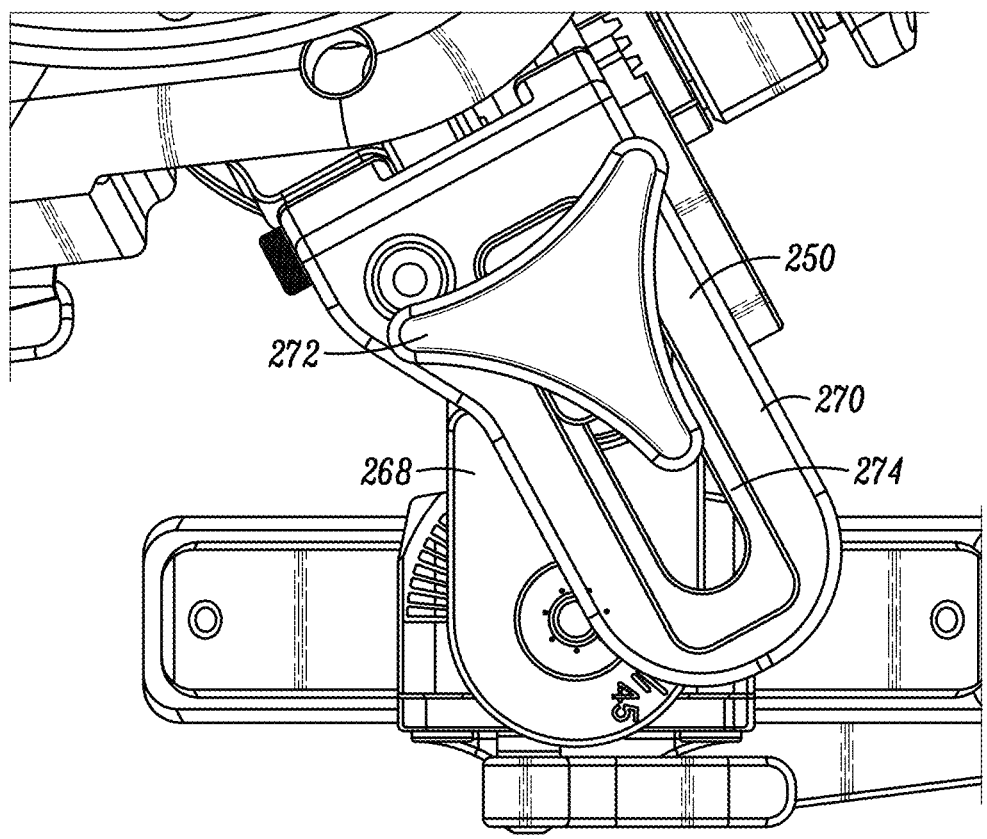
FIG. 14 is a close-up view depicting the shoulder width adjustment mechanism of FIG. 11.

With additional reference to FIG. 14, the shoulder width adjustment mechanism 250 can include a first member 268 operably coupled to a second member 270, for example via an adjustment knob 272 or other fastener. In some embodiments, at least one of the first member 268 or second member 270 can include structure defining a slot 274 in which a portion of the adjustment knob 272 can traverse, thereby enabling a sliding translation of the first member 268 relative to the second member 270. The translational shift of the first member 268 relative to the second member 270 can be locked in position, for example via tightening of the adjustment knob 272. Accordingly, in some embodiments, the shoulder width adjustment mechanism 250 can be configured to account for varying shoulder widths and other physiological differences in patients. In one embodiment, the shoulder width adjustment mechanism 250 can be configured to enable a lateral shifting of the limb augmentation portion 104 outwardly from the limb augmentation support member 140 by a distance of approximately 1.25 inches; although other lateral extension distances are also contemplated.

Figure 15:
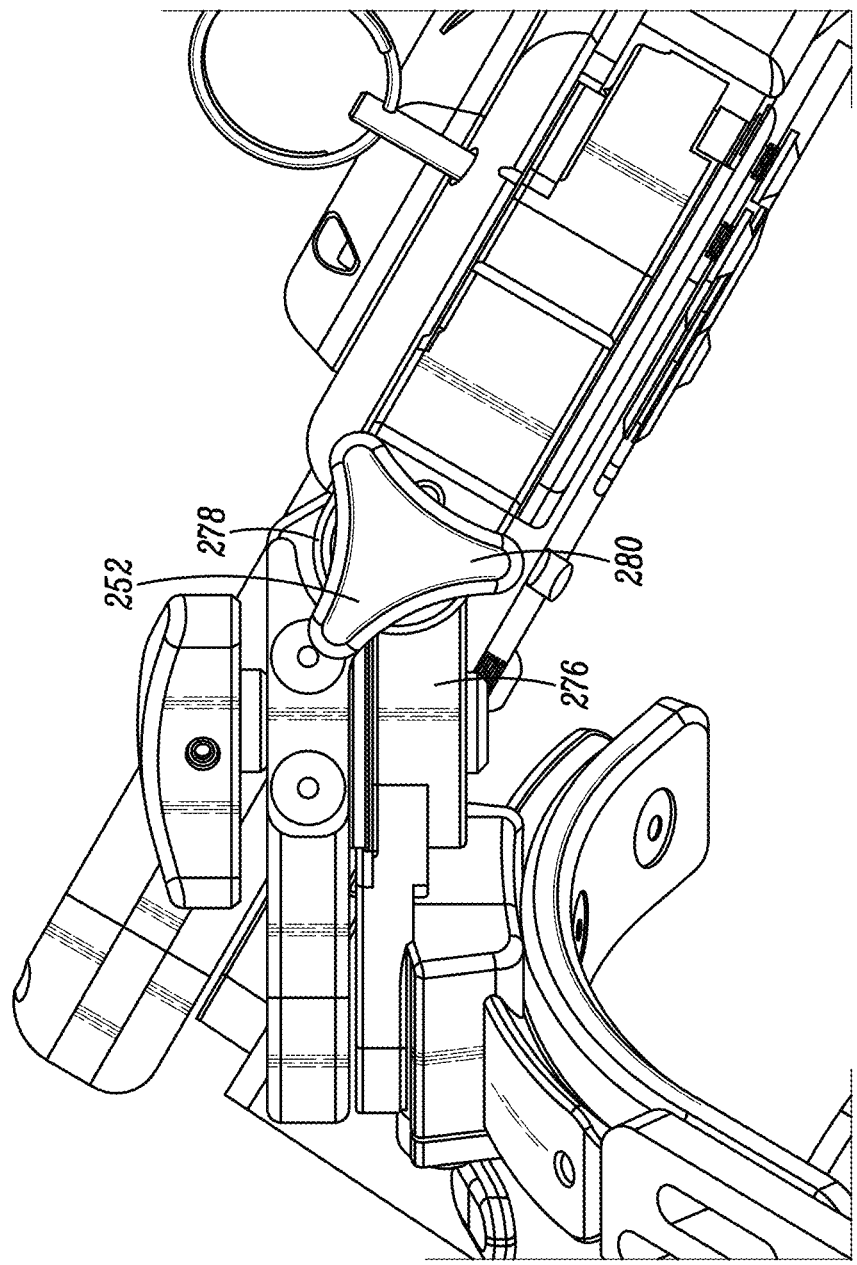
FIG. 15 is a close-up view depicting the shoulder abduction/adduction angle adjustment mechanism of FIG. 11.

With additional reference to FIG. 15, the shoulder abduction/adduction angle adjustment mechanism 252 can include a first member 276 operably pivotably coupled to a second member 278, for example via an adjustment knob 280 or other fastener. The pivotable coupling of the first member 276 relative to the second member 278 can be locked in position, for example via tightening of the adjustment knob 280. Accordingly, in some embodiments, the shoulder abduction/adduction angle adjustment mechanism 252 can be configured to selectively position of the limb augmentation portion 104 relative to the limb augmentation support member 140 at a desirable an abduction/adduction angle to accommodate the function of the anticipated usage of the upper torso orthotic device 100 by a patient. In one embodiment, the shoulder abduction/adduction angle adjustment mechanism 252 can be configured to adjust the angle of the limb augmentation portion 104 relative to the limb augmentation support member 140 through a range of about 60° (e.g., from about 15° to about 75°); although other angular ranges are also contemplated. In some embodiments, the abduction/adduction angle can be adjustable in discrete increments (e.g., 15° increments within the range of about 60°).

A table listing several of the above-mentioned component sizes and adjustment mechanisms enabling the upper torso orthotic device 100 to be adapted to a wide variety of body shapes, sizes and augmentation needs of patients or users follows:

TABLE 1

| Orthotic Adjustment | Anticipated Frequency | Adjustment Type |
| --- | --- | --- |
| Vest Portion (Size) | Once | Proper Fitting |
| LSO Portion (Size) | Once | Proper Fitting |
| Semi-rigid Support Members (Size) | Once | Proper Fitting |
| Inflatable Bolsters | Daily | Proper Fitting/Improved Function |
| Back Rails (Size) | Once | Proper Fitting |
| Lateral Adjustment Mechanism | As Needed | Proper Fitting/Improved Function |
| Height Adjustment Mechanism | As Needed | Proper Fitting/Improved Function |
| Shoulder Positioning Mechanism | As Needed | Proper Fitting/Improved Function |
| Humeral Cuff (Size) | Once | Proper Fitting |
| Elbow Cuff (Size) | Once | Proper Fitting |
| Forearm Cuff (Size) | Once | Proper Fitting |
| Length of Upper Arm Assembly | Once | Proper Fitting |
| Leveling mechanism | Daily | Improved Function |
| Clavicle Retraction/Protraction Angle Adjustment Mechanism | As Needed | Proper Fitting/Improved Function |
| Shoulder With Adjustment Mechanism | Daily | Proper Fitting/Improved Function |
| Shoulder Abduction/Adduction Angle Adjustment Mechanism | Daily | Proper Fitting/Improved Function |

Figure 16:
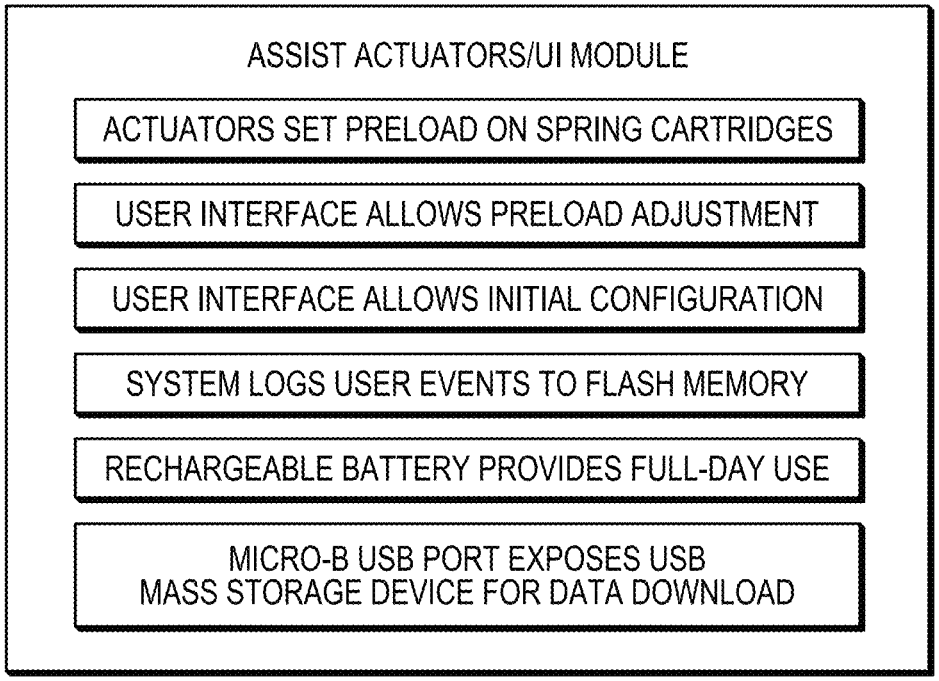
FIG. 16 is a flowchart for an assist actuator/user interface module, in accordance with an embodiment of the disclosure.

With reference to FIG. 16, in some embodiments, the output of the assisted force mechanisms 186, 188 (e.g., tension in the spring cartridges 206, 220) can be calibrated by or one or more Bowden cables 136A/B (as depicted in FIG. 1) operably coupled to one or more powered actuators. For example, in one embodiment, software can enable the calibration to account for varying degrees of desirable output of the assisted force mechanisms 186, 188; for example between a low, medium and high output to account for varying anticipated loads likely to be experienced by the upper torso orthotic device 100. In some embodiments, software can also track when the upper torso orthotic device 100 is powered on and off, and when the levels of output assistance are changed. Accordingly, in some embodiments, the upper torso orthotic device 100 acts as a hybrid system wherein the assisted force mechanisms 186, 188 include both a passive element (e.g., spring force) and an actively powered element (e.g., manipulation from one or more actuators).

Figure 17:
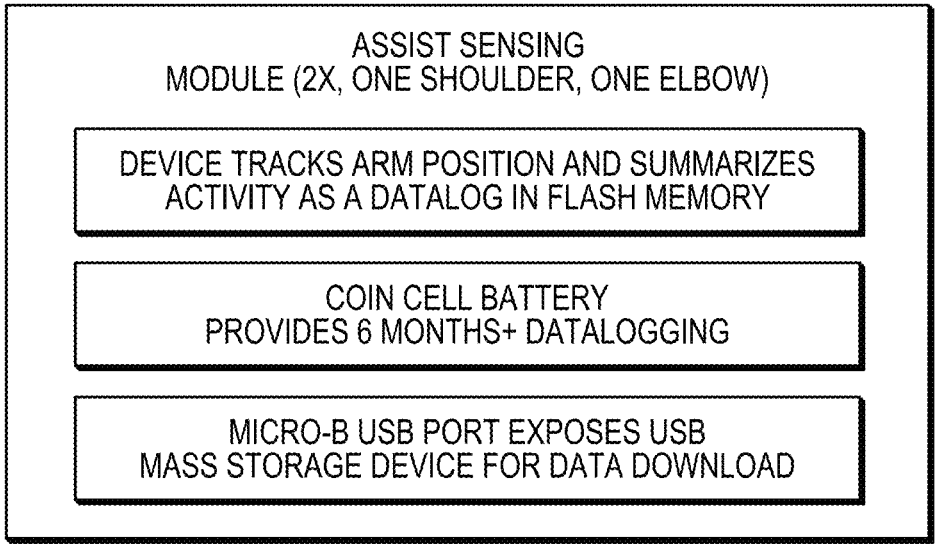
FIG. 17 is a flowchart for an assist sensing module, in accordance with an embodiment of the disclosure.

With reference to FIG. 17, at least one of the shoulder assembly 180 and elbow assembly 184 can include a positional sensor configured to track pivotal rotation of the respective shoulder and elbow of a patient during use. In some embodiments, the sensors can be ultralow power sensors capable of tracking the degrees of movement in the joints. Data gathered by the sensors can include the rate of change, total degrees moved, number of times moved, and the time that the movement occurred.

It should be understood that the individual steps used in the methods of the present teachings may be performed in any order and/or simultaneously, as long as the teaching remains operable. Furthermore, it should be understood that the apparatus and methods of the present teachings can include any number, or all, of the described embodiments, as long as the teaching remains operable.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

What is claimed is:

1. An adjustable shoulder assembly for an upper torso wearable orthotic device configured to enable an above shoulder mounted limb augmentation member to be selectively adjustable to account for differences in anatomical fit and function of a range of different users, the adjustable shoulder assembly comprising:
a leveling mechanism including structure configured to enable sliding adjustment of a limb augmentation member relative to a curved rail of a support frame member of the orthotic device to adjust an orientation of the limb augmentation member relative to a gravitational frame of reference as detected by the leveling mechanism;
a clavicle retraction/protraction angle adjustment mechanism including structure configured to enable angular adjustment of the limb augmentation member relative to the support frame member to account for anatomical differences among the range of different users, the clavicle retraction/protraction angle adjustment mechanism including a first clavicle retraction/protraction angle adjustment member pivotably coupled to a second clavicle retraction/protraction angle adjustment member via at least one clavicle retraction/protraction angle adjustment fastener, wherein selective tightening of the at least one clavicle retraction/protraction angle adjustment fastener enables locking of the first clavicle retraction/protraction angle adjustment member relative to the second clavicle retraction/protraction angle adjustment member, and wherein the clavicle retraction/protraction angle adjustment mechanism further includes a plurality of ratcheting detents configured to aid in alignment of the first clavicle retraction/protraction angle adjustment member relative to the second clavicle retraction/protraction angle adjustment member along specific angle increments;
a shoulder abduction angle adjustment mechanism including structure configured to enable positioning of the limb augmentation member at a desired abduction angle relative to the support frame member; and
a shoulder width adjustment mechanism including structure configured to enable lateral translation of the limb augmentation member relative to the support frame member to account for at least one of changes in the adduction angle of the limb augmentation member relative to the support frame member and anatomical differences among the range of different users.

2. The adjustable shoulder assembly of claim 1, wherein the leveling mechanism includes a leveling mechanism bracket slidably couplable to the curved rail of the support frame member.

3. The adjustable shoulder assembly of claim 2, wherein the leveling mechanism further includes a leveling mechanism quick release member configured to enable selective locking of the leveling mechanism bracket relative to the support frame member.

4. The adjustable shoulder assembly of claim 1, wherein the shoulder abduction angle adjustment mechanism includes a first shoulder abduction angle adjustment member pivotably coupled to a second shoulder abduction angle adjustment member via at least one shoulder abduction angle adjustment knob, wherein selective tightening of the shoulder abduction angle adjustment knob enables locking of the first shoulder abduction angle adjustment member relative to the second shoulder abduction angle adjustment member.

5. The adjustable shoulder assembly of claim 4, wherein the shoulder abduction angle adjustment mechanism is configured to enable adjustment of the shoulder abduction angle of the limb augmentation member relative to the support frame member in discrete angle increments through a range of about 60 degrees.

6. The adjustable shoulder assembly of claim 1, wherein the shoulder width adjustment mechanism includes a first shoulder width adjustment member slidably coupled to a second shoulder width adjustment member.

7. The adjustable shoulder assembly of claim 6, wherein the shoulder width adjustment mechanism further includes structure defining a slot in which a shoulder width adjustment knob is configured to traverse, wherein the shoulder width adjustment knob is configured to selectively lock the first shoulder width adjustment member in position relative to the second shoulder width adjustment member.

8. An upper torso wearable orthotic device having multiple adjustment mechanisms configured to enable adaptation to a wide variety of body shapes, sizes and augmentation needs of a user, the upper torso wearable orthotic device comprising:
 a body worn support frame member configured to dynamically distribute a weight of the upper torso orthotic device across an upper torso of the user; and
 a limb augmentation member configured to augment a native strength of an arm of the user by overcoming the effects of gravity, the limb augmentation member including an adjustable shoulder assembly, the adjustable shoulder assembly including —
  a leveling mechanism including structure configured to enable sliding adjustment of the limb augmentation member relative to the support frame member;
  a shoulder abduction angle adjustment mechanism including structure configured to enable positioning of the limb augmentation member at a desired abduction angle relative to the support frame member, wherein the shoulder abduction angle adjustment mechanism includes a first shoulder abduction angle adjustment member pivotably coupled to a second shoulder abduction angle adjustment member via at least one shoulder abduction angle adjustment knob, wherein selective tightening of the shoulder abduction angle adjustment knob enables locking of the first shoulder abduction angle adjustment member relative to the second shoulder abduction angle adjustment member; and
  a shoulder width adjustment mechanism including structure configured to enable lateral translation of the limb augmentation member relative to the support frame.

9. The upper torso wearable orthotic device of claim 8, wherein the leveling mechanism includes a leveling mechanism bracket slidably couplable to a curved rail of the body worn support frame member.

10. The upper torso wearable orthotic device of claim 9, wherein the leveling mechanism further includes a leveling mechanism quick release member configured to enable selective locking of the leveling mechanism bracket relative to the support frame member.

11. The upper torso wearable orthotic device of claim 8, wherein the shoulder abduction angle adjustment mechanism is configured to enable adjustment of the shoulder abduction angle of the limb augmentation member relative to the body worn support frame member in discrete angle increments through a range of about 60 degrees.

12. The upper torso wearable orthotic device of claim 8, wherein the shoulder width adjustment mechanism includes a first shoulder width adjustment member slidably coupled to a second shoulder width adjustment member.

13. The upper torso wearable orthotic device of claim 12, wherein the shoulder width adjustment mechanism further includes structure defining a slot in which an shoulder width adjustment knob is configured to traverse, wherein selective tightening of the shoulder width adjustment knob enables locking of the first shoulder width adjustment member relative to the second shoulder width adjustment member.

14. The upper torso wearable orthotic device of claim 8, wherein the body worn support frame member includes a body frame portion constructed of a semi-rigid material having one or more sets of living hinges configured to enable the body frame portion to readily conform to the upper torso of the user.

15. The upper torso wearable orthotic device of claim 14, wherein the body frame portion includes one or more airflow channels configured to encourage air circulation around the user during use.

16. The upper torso wearable orthotic device of claim 8, wherein the body worn support frame member includes one or more inflatable bolsters configured to aid in more evenly distributing a weight of the upper torso orthotic device across the upper torso of the user.

17. A method of adjusting an above shoulder mounted limb augmentation member of an upper torso wearable orthotic device relative to a support frame member, the method comprising:
 leveling the limb augmentation member relative to a gravitational frame of reference by sliding the limb augmentation member along a curved rail of the support frame member;
 adjusting a clavicle retraction/protraction angle of the limb augmentation member relative to the support frame member by a clavicle retraction/protraction angle adjustment mechanism, the clavicle retraction/protraction angle adjustment mechanism including a first clavicle retraction/protraction angle adjustment member pivotably coupled to a second clavicle retraction/protraction angle adjustment member via at least one clavicle retraction/protraction angle adjustment fastener, wherein selective tightening of the clavicle retraction/protraction angle adjustment fastener enables locking of the first clavicle retraction/protraction angle adjustment member relative to the second clavicle retraction/protraction angle adjustment member, and wherein the clavicle retraction/protraction angle adjustment mechanism further includes a plurality of ratcheting detents configured to aid in alignment of the first clavicle retraction/protraction angle adjustment member relative to the second clavicle retraction/protraction angle adjustment member along specific angle increments;
 adjusting a shoulder abduction angle of the limb augmentation member relative to the support frame member; and
 adjusting a lateral extension distance of the limb augmentation member relative to the support frame member.

* * * * *